(12) United States Patent
Yuan

(10) Patent No.: US 7,196,093 B2
(45) Date of Patent: Mar. 27, 2007

(54) REVERSIBLE INHIBITORS OF SAH HYDROLASE AND USES THEREOF

(75) Inventor: Chong-Sheng Yuan, San Diego, CA (US)

(73) Assignee: General Atomics, San Diego, CA (US)

( * ) Notice: Subject to any disclaimer, the term of this patent is extended or adjusted under 35 U.S.C. 154(b) by 5 days.

(21) Appl. No.: 10/410,879

(22) Filed: Apr. 9, 2003

(65) Prior Publication Data

US 2004/0204429 A1    Oct. 14, 2004

(51) Int. Cl.
- C07D 473/34  (2006.01)
- C07D 487/04  (2006.01)
- A61K 31/52  (2006.01)
- A61P 31/14  (2006.01)
- A61P 35/00  (2006.01)

(52) U.S. Cl. .............. 514/263.38; 514/263.4; 514/303; 544/276; 544/277; 546/116

(58) Field of Classification Search ........... 514/263.38, 514/263.4, 303; 544/276, 277; 546/116
See application file for complete search history.

(56) References Cited

U.S. PATENT DOCUMENTS

| | | | |
|---|---|---|---|
| 5,593,990 A | 1/1997 | D'Amato | 514/235.2 |
| 5,629,327 A | 5/1997 | D'Amato | 514/323 |
| 5,641,783 A | 6/1997 | Klein et al. | |
| 5,668,173 A | 9/1997 | Garrow | 514/557 |
| 5,686,102 A | 11/1997 | Gross et al. | 424/450 |
| 5,712,291 A | 1/1998 | D'Amato | 514/323 |
| 5,736,154 A | 4/1998 | Fuisz | 424/449 |
| 5,741,511 A | 4/1998 | Lee et al. | 424/449 |
| 5,756,466 A | 5/1998 | Bemis et al. | 514/18 |
| 5,854,023 A | 12/1998 | Hillman et al. | 435/69.1 |
| 5,869,305 A | 2/1999 | Samulski et al. | 435/172.3 |
| 5,886,039 A | 3/1999 | Kock et al. | 514/557 |
| 5,888,767 A | 3/1999 | Dropulić et al. | 435/69.1 |
| 5,941,868 A | 8/1999 | Kaplan et al. | 604/500 |
| 5,962,274 A | 10/1999 | Parks | 435/91.1 |
| 6,020,337 A | 2/2000 | Leigh et al. | |
| 6,066,467 A | 5/2000 | Xu et al. | |
| 6,133,274 A | 10/2000 | Underiner et al. | |
| 6,197,801 B1 | 3/2001 | Lin | 514/365 |
| 6,203,818 B1 | 3/2001 | Vester | 424/569 |
| 6,210,686 B1 | 4/2001 | Bell et al. | 424/400 |
| 6,258,374 B1 | 7/2001 | Friess et al. | 424/436 |
| 6,274,170 B1 | 8/2001 | Heibel et al. | 424/458 |
| 6,323,188 B1 | 11/2001 | Weissman | 514/52 |
| 6,353,003 B1 | 3/2002 | Anderson | 514/324 |
| 6,361,800 B1 | 3/2002 | Cooper et al. | 424/630 |
| 2002/0044919 A1 | 4/2002 | Yu | 424/85.1 |
| 2005/0182075 A1* | 8/2005 | Yuan | 514/263.2 |

FOREIGN PATENT DOCUMENTS

GB    1330704 A  *  9/1773

GB    1330704    9/1973

OTHER PUBLICATIONS

Hana Dvorakova, et al., Collection of Czechoslovak Chemical Communications 1993, 58(3), 629-648.*
Autoimmunity, Methods and Protocols, Chapter 19, pp. 365-375 in Methods in Molecular Medicine, vol. 102, Ed. by A. Perl , Human Press, 2004.*

(Continued)

*Primary Examiner*—Mark L. Berch
(74) *Attorney, Agent, or Firm*—Morrison & Foerster LLP

(57) ABSTRACT

1. The present invention provides compositions and methods for reversibly inhibiting S-adenosyl-L-homocysteine (SAH) hydrolase. The compounds of the present invention can be used as an anti-hemorrhagic viral infection agent, an immunosuppressant, a homocysteine lowering agent, or an anti-neoplasm agent. The compositions and methods of the present invention can be used for the prevention and treatment of hemorrhagic virus infection, autoimmune diseases, autograft rejection, neoplasm, hyperhomocysteineuria, cardiovascular disease, stroke, Alzheimer's disease, multiple sclerosis or diabetes. The compound of the present invention and/or used in the present invention has the formula (I):

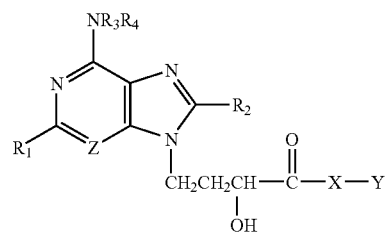

wherein Z is selected from the group consisting of carbon and nitrogen,

R1 and R2 are the same or different, and are selected from the group consisting of hydrogen, hydroxy, alkyl, cycloalkyl, alkenyl, alkoxy, amino, aryl, heteroaryl, and halogen;

R3 and R4 are the same or different and are selected from the group consisting of hydrogen, alkyl, acetyl, alkenyl, aryl, and heteroaryl;

X is selected from the group consisting of oxygen, nitrogen, and sulfur; and

Y is selected from the group consisting of hydrogen, a $C_{1-10}$ alkyl group, alkenyl, vinyl, aryl, and heteroaryl, provided that the compound is not (4-adenine-9-yl)-2-hydroxybutanoic acid.

13 Claims, 8 Drawing Sheets

OTHER PUBLICATIONS

't Hart et al. Drug Discovery Today 9: 517-524 (2004).*
Dictionary of Biochemistry and Molecular Biology, Second Ed., (John Wiley & Sons, 1989) p. 417.*
Association of the British Pharmaceutical Industry, "Target Crohn's and Colitis: Inflammatory Bowel Disease and the Pharmaceutical Industry- Future Medicines in the Development Pipeline" at <http://www.abpi.org.uk> (visited Feb. 4, 2003).
Auerbach and Auerbach, "Angiogenesis Inhibition: A Review" Pharmacol. Ther. 63:265-311 (1994).
Bao, L. et al., "The Critical Role of IL-12p40 in Initiating, Enhancing, and Perpetuating Pathogenic Events in Murine Experimental Autoimmune Neuritis" [Abstract] at <http://www.brainpathology.com> (visited Feb. 4, 2003).
Bartlett et al., "CAVEAT: A Program to Facilitate the Structure-Derived Design of Biologically Active Molecules" *In Molecular Recognition in Chemical and Biological Problems*, Special Pub., Royal Chem. Soc. 78:182-196 (1989).
Bohm, "The Computer Program LUDI: A New Method for the De Novo Design of Enzyme Inhibitors" J. Comp. Aid. Molec. Design 6:61-78 (1992).
Brooks et al., "CHARMM: A Program for Macromolecular Energy, Minimization, and Dynamics Calculations" J Comp. Chem. 4(2):187-217 (1983).
Cerino, V., "UNMC Dentistry Researchers Receive $209,000 Grant to Study Role of Protein in Multiple Sclerosis" at <http://www.unmc.edu/News/petro.htm> (visited Feb. 4, 2003).
Chem. Abstr. 1972:514811 (Abstract to JP47-023550).
Cohen et al., J. Med. Chem. 33:883-894 (1990).
Commission of Biochemical Nomenclature, "IUPAC-IUB Commission on Biochemical Nomenclature Symbols for Amino-Acid Derivatives and Peptides Recommendations (1971)" Biochemistry 11:1726-1732 (1972).
Coulter-Karis and Hershfield, "Sequence of Full Length cDNA for Human S-Adenosylhomocysteine Hydrolase" Ann. Hum. Genet. 53(2):169-175 (1989).
Gewolb, J., "New Diabetes Gene Found" at <http://bric.postech.ac.kr/science/97now/01_1now/010130a.html> (visited Feb. 4, 2003).
Goodford, "A Computational Procedure for Determining Energetically Favorable Binding Sites on Biologically Important Macromolecules" J. Med. Chem. 28:849-857 (1985).
Goodman and Gilman, *The Pharmacological Basis of Therapeutics*, (9th ed.), McGraw-Hill pp. 1294-1304 (1996).
Goodsell et al., "Automated Docking of Substrates to Proteins by Simulated Annealing" Proteins: Structure, Function and Genetics 8:195-202 (1990).
Holy et al., "Structure-Activity Studies on Open-Chain Analogues of Nucleosides: Inhibition of S-Adenosyl-L-Homocysteine Hydrolase and Antiviral Activity" Coll. Czechoslovak Chem. Commun. 50:262-279 (1985).
Holy, Coll. Czech. Chem. Commun. 43:3444-3464 (1978).
Hopfinger et al., *In Concepts and Applications of Molecular Similarity* Johnson and Maggiora (eds.), Wiley (1990).
Kirkman, R., "Protein Design Labs (PDLI) Begins Phase I Clinical Trial of SMART Anti-IL-12 Antibody" at <http://www.biospace.com/news_story.cfm?storyID=9223720&full=1> (visited Feb. 4, 2003).

Klebe, G., "Recent Developments in Structure-Based Drug Design" J. Mol. Med. 78:269-281 (2000).
Kuntz et al., "A Geometric Approach to Macromolecule-Ligand Interactions" J. Mol. Biol. 161:269-288 (1982).
Maignan et al., Curr. Top. Med. Chem. 1:161-174 (2001).
Marshall, Ann. Ref. Pharmacol. Toxicol. 27:193 (1987).
Martin, "3D Database Searching in Drug Design" J. Med. Chem. 35(12):2145-2154 (1992).
Mayer et al., J. Comp. Aided Molec. Design 1:3-16 (1987).
Merta, A. et al., "S-Adensoyl-L-Homocysteine Hydrolase from Mouse Leukemic Cells: Isolation and Properties" Coll. Czech. Chem. Commun. 48:2701-2708 (1983).
Miranker et al., "Functionality Maps of Binding Sites: A Multiple Copy Simultaneous Search Method" Proteins: Structure, Function and Genetics 11:29-34 (1991).
National Institute of Health, "Understanding Autoimmune Disease" at <http://www.niaid.nih.gov/publications/autoimmune/autoimmune.htm> (visited Apr. 10, 2003).
Navia et al., Curr. Opin. Struc. Biol. 2:202-210 (1991).
Nishibata et al., "Automatic Creation of Drug Candidate Structures Based on Receptor Structure. Starting Point for Artificial Lead Generation" Tetrahedron 47(43):8985-8990 (1991).
O'Reilly, M., "The Preclinical Evaluation of Angiogenesis Inhibitors" Investigational New Drugs 15:5-13 (1997).
Schanche, et al., "The Effect of Aliphatic Adenine Analogues on S-Adenosylhomocysteine and S-Adenosylhomocysteine Hydrolase in Intact Rat Hepatocytes" Molecular Pharmacology 26:553-558 (1984).
Seshadri et al., "Plasma Homocysteine As a Risk Factor for Dementia and Alzheimer's Disease" N. Eng. J. Med. 46:476-483 (2002).
Simpson et al., "Spectrophotometric Determination of Lymphocyte Mediated Sheep Red Blood Cell Hemolysis In Vitro" J. Immunol. Methods 21:159-165 (1978).
Steinman, L., "Multiple Sclerosis: A Two-Stage Disease" 2001 Nature Publishing Group http://immunol.nature.com.
Votruba and Holy, "Eritadenines- Novel Type of Potent Inhibitors of S-Adenosyl-L-Homocysteine Hydrolase" Coll. Czech. Chem. Commun. 47:167-172 (1982).
Votruba and Holy, Coll. Czech Chem. Commun. 45:3039 (1980).
Weiner et al.,"A New Force Field for Molecular Mechanical Simulation of Nucleic Acids and Proteins" J. Am. Chem Soc. 106:765-784 (1984).
Wolfe and Borchardt, "S-Adenosyl-L-Homocysteine Hydrolase as a Target for Antiviral Chemotherapy" Journal of Medicinal Chemistry 34(5):1521-1530 (1991).
Yuan et al., Exp. Opin. Ther. Patents 9:1197-1206 (1999).
Yuan, C. et al., "Design and Synthesis of S-Adenosylhomocysteine Hydrolase Inhibitors As Broad-Spectrum Antiviral Agents" *In Antiviral Drug Des.*, De Clerq (ed.), JAI Press, Inc. London UK 2:41-88 (1996).
Ziegler, J., "Angiogenesis Research Enjoys Growth Spurt in the 1990s" J. Nat'l Cancer Inst. 88:786-788 (1996).
International Search Report for PCT/US04/11229, mailed on Aug. 17, 2005, 4 pages.
Wolos et al., J. Immunology (1993) 150(8):3264-3273.

* cited by examiner

A

Control | DZ2002 0.1μmol/L
DZ2002 1μmol/L | DZ2002 10 μmol/L

B

Control | DZ2002 0.1μmol/L
DZ2002 1μmol/L | DZ2002 10 μmol/L

REVERSIBLE INHIBITORS OF SAH HYDROLASE AND USES THEREOF

BACKGROUND OF THE INVENTION

SAH hydrolase has been an attractive target for antiviral drug design based on the observation that many viruses require 5'-capped, methylated structures on their mRNA for efficient translation of viral proteins. Yuan et al., *Exp. Opin. Ther. Patents*, 9: 1197–1206 (1999); Yuan et al., in *Adv. Antiviral Drug Des*. vol 2, pp. 41–88, De Clercq (ed)., JAI Press, Inc. London, UK (1996). Inhibition of SAH hydrolase results in inhibition of S-adenosyl-L-methionine (SAM)-dependent methylation reactions, including viral mRNA methylation, thus inhibiting viral replication (Scheme 1).

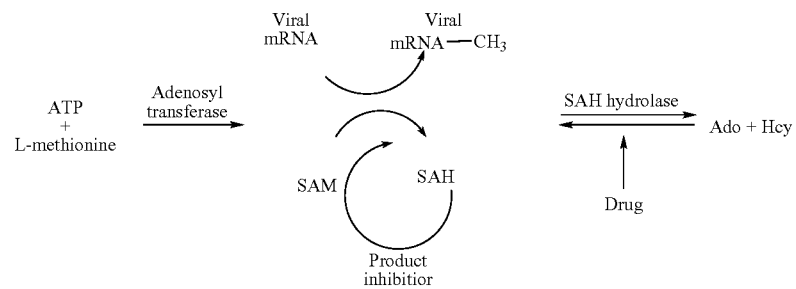

Scheme 1. Mechanism of Methylation Based Inhibition of Viral Replication

Numerous inhibitors of SAH hydrolase have been identified from naturally occurring compounds and synthetic compounds. Most potent inhibitors are irreversible inhibitors, which irreversibly inactivate SAH hydrolase in a time-dependent fashion. Studies have demonstrated that irreversible inhibitors only produce narrow therapeutic windows due to their severe cytotoxic effects (Wolfe and Borchardt, *Journal of Medicinal Chemistry*, 34:1521–1530 (1991)). Since SAH hydrolase is a ubiquitous cellular enzyme with a very slow turnover rate ($t_{1/2}$ =24 hours in mouse liver), irreversible inhibitors can cause prolonged inhibition of the enzyme activity. For instance, it can take up to seven days for complete recovery of enzyme activity, which can lead to unwanted side effects. The severe cytotoxicity associated with irreversible inhibitors has been the major factor that has impaired the development of these inhibitors into clinically useful drugs. Because of the cytotoxicity associated with irreversible inhibitors, reversible inhibitors are preferred.

However, at present, there are no known reversible SAH hydrolase inhibitors that are potent enough to produce substantial inhibitory activity against the enzyme when tested in vivo. For example, the reversible inhibitor (S)-9-(2,3-dihydroxypropyl)adenine ((S)-DHPA), which has a $K_i$ value of 3.5 μM against SAH hydrolase, lacks inhibitory potency. (Votruba and Holy, *Coll. Czech. Chem. Commun.*, 45:3039 (1980)). Though (s)-DHPA was reported to be a reversible inhibitor of isolated AdoHcy hydrolase (Votruba and Holy, *Coll. Czech. Chem. Commun.*, 45:3039 (1980)), it was also reported to be a irreversible inhibitor of intracellular AdoHcy hydrolase (Schanche et al., *Molecular Pharmacology*, 26:553–558 (1984)). Thus, existing reversible inhibitors are not clinically useful therapeutic agents, and there remains a need for SAH hydrolase inhibitors that exhibit potency without the undesired cytotoxic effects.

BRIEF SUMMARY OF THE INVENTION

The present invention provides novel reversible inhibitors of SAH hydrolase. The compounds of the present invention are useful as agents demonstrating biological activities related to their ability to inhibit SAH hydrolase. In one embodiment, the reversible inhibitors of SAH hydrolase have the formula (I), and pharmaceutically acceptable salts thereof:

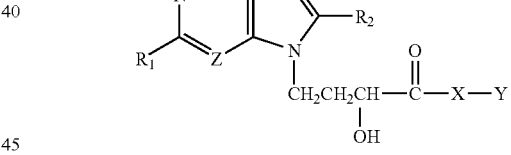

wherein Z is carbon or nitrogen, R1 and R2 are the same or different, and are hydrogen, hydroxy, alkyl, cycloalkyl, alkenyl, alkoxy, amino, aryl, heteroaryl, or halogen; R3 and R4 are the same or different and are hydrogen, alkyl, acetyl, alkenyl, aryl, or heteroaryl; X is oxygen, nitrogen, or sulfur; and Y is hydrogen, a $C_{1-10}$ alkyl group, alkenyl, vinyl, aryl, or heteroaryl. In a particular embodiment, the compound is not (4-adenine-9-yl)-2-hydroxybutanoic acid.

Compounds of formula I can have an S configuration at the β carbon, an R configuration at the β carbon, or comprise a racemic mixture. In one embodiment, the compounds have a $K_i$ value less than 100 nM for a mammalian SAH hydrolase in a biological medium, e.g., serum. In other embodiments, the compounds have a $K_i$ value between about 1 nM and about 100 nM for a mammalian SAH hydrolase in a biological medium. The compounds preferably have a $K_i$ value less than 100 nM, or a $K_i$ value between about 1 nM and about 100 nM for a human SAH hydrolase in a biological medium.

Compounds of formula I can have substituents wherein R1, R2, R3, and R4 are hydrogen. In one aspect of the present invention, X is oxygen. In another aspect of the present invention, Y is hydrogen or a $C_{1-10}$ alkyl group. In yet another aspect of the present invention, R1, R2, R3, and R4 are hydrogen, X is oxygen, and Y is hydrogen or a $C_{1-10}$ alkyl group.

The present invention also relates to a pharmaceutical composition comprising an effective amount of a compound of formula I or pharmaceutically acceptable salts thereof, and a pharmaceutically acceptable carrier or diluent. Pharmaceutical compositions may be administered by oral, parenteral (e.g., intramuscular, intraperitoneal, intravenous, intracisternal injection or infusion, subcutaneous injection, or implant), inhalation spray, nasal, vaginal, rectal, sublingual, or topical routes of administration. The pharmaceutical compositions may be formulated in suitable dosage unit formulations appropriate for each route of administration.

It is not intended that the present invention be limited to particular formulations or particular modes of administration. In one embodiment, the composition is formulated for oral, parenteral, intranasal, topical, or injectable administration. Non-limited examples of injectable administration are intracavernous injection, subcutaneous injection, intravenous injection, intramuscular injection and intradermal injection. The pharmaceutical composition can be formulated for oral administration in a dosage ranging from about 0.1 to about 20 mg/kg per day. The pharmaceutical composition can also be formulated for injectable administration in a dosage ranging from about 0.1 to about 20 mg/kg per day.

Pharmaceutical compositions of the present invention can be formulated in a solid or liquid dosage form. For example, the pharmaceutical compositions may be formulated as a solid in the form of tablets, capsules, granules, powders, and similar compounds. The pharmaceutical compositions may also be formulated as a liquid in the form of syrups, injection mixtures, and the like.

The present invention also provides a kit comprising an effective amount of the composition of the present invention, and an instruction means for administering the composition.

Furthermore, the present invention provides methods for reversibly inhibiting the activity of a S-adenyl-L-homocysteine (SAH) hydrolase. In one embodiment, the present invention provides a method for reversibly inhibiting activity of a S-adenosyl-L-homocysteine (SAH) hydrolase in a mammal, comprising administering to a mammal to which such reversible inhibition is needed or desirable, an effective amount of a compound or a pharmaceutically acceptable salt thereof, having the formula (I):

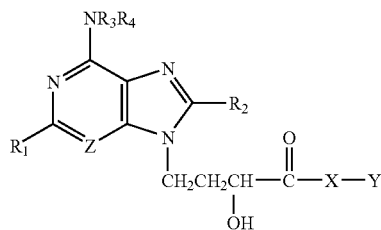

wherein Z is selected from the group consisting of carbon and nitrogen, R1 and R2 are the same or different, and are selected from the group consisting of hydrogen, hydroxy, alkyl, cycloalkyl, alkenyl, alkoxy, amino, aryl, heteroaryl, and halogen; R3 and R4 are the same or different and are selected from the group consisting of hydrogen, alkyl, acetyl, alkenyl, aryl, and heteroaryl; X is selected from the group consisting of oxygen, nitrogen, and sulfur; and Y is selected from the group consisting of hydrogen, a $C_{1-10}$ alkyl group, alkenyl, vinyl, aryl, and heteroaryl, thereby reversibly inhibiting the activity of SAH hydrolase in said mammal. In a particular embodiment, the administered compound or a pharmaceutically acceptable derivative thereof is not (4-adenine-9-yl)-2-hydroxybutanoic acid.

In preferred embodiments, the mammal is suspected of having a disease selected from the group consisting of hemorrhagic viral infection, autoimmune disease, autograft rejection, neoplasm, hyperhomocysteineuria, cardiovascular disease, stroke, Alzheimer's disease, diabetes, inflammatory Bowel disease, multiple sclerosis and autoimmune neuritis. However, it is not intended that the present invention be limited to the prevention and treatment of particular diseases.

It is an object of the present invention to provide methods for preventing and treating hemorrhagic viral infections. In one aspect, the method comprises administering an effective amount of compounds having formula I in the treatment of hemorrhagic viral infections in a mammal. In particular embodiments, the hemorrhagic viral infection is caused by a virus selected from the group consisting of a Bunyaviridaea, a Filoviridae, a Flaviviridae, and an Arenaviridae virus. In other particular embodiments, the Filoviridae virus is Ebola virus.

It is also an object of the present invention to provide methods for preventing and treating autoimmune diseases. In one aspect, the method comprises administering an effective amount of compounds having formula I in the treatment of an autoimmune disease in a mammal.

It is also an object of the present invention to provide methods for preventing and treating allograft rejection. In one aspect, the method comprises administering an effective amount of compounds having formula I in the treatment of allograft rejection in a mammal.

Furthermore, it is an object of the present invention to provide methods for preventing or treating hyperhomocysteineuria, or for lowering plasma homocysteine in a mammal. In one aspect, the method comprises administering an effective amount of compounds having formula I for lowering plasma homocysteine in a mammal.

Further, it is an object of the present invention to provide methods for preventing or treating neoplasm. In one aspect, the method comprises administering an effective amount of compounds having formula I for in the treatment of neoplasm in a mammal. Non-limiting examples of neoplasm are neoplasm of the adrenal gland, anus, auditory nerve, bile ducts, bladder, bone, brain, breast, bruccal, central nervous system, cervix, colon, ear, endometrium, esophagus, eye, eyelids, fallopian tube, gastrointestinal tract, head and neck, heart, kidney, larynx, liver, lung, mandible, mandibular condyle, maxilla, mouth, nasopharynx, nose, oral cavity, ovary, pancreas, parotid gland, penis, pinna, pituitary, prostate gland, rectum, retina, salivary glands, skin, small intestine, spinal cord, stomach, testes, thyroid, tonsil, urethra, uterus, vagina, vestibulocochlear nerve, and the vulva.

The present invention also provides a combination, comprising an effective amount of a compound having formula I, and an effective amount of an anti-hemorrhagic viral infection agent, an immunosuppressant, a plasma homocysteine lowering agent, and an anti-neoplasm agent. The combination can further comprise a pharmaceutically acceptable carrier or excipient. In a particular embodiment, the combination does not include (4-adenine-9-yl)-2-hydroxybutanoic acid.

In a particular embodiment, the anti-hemorrhagic viral infection agent inhibits interleukin-1 (IL-1), tumor necrosis factor (TNF), or a combination thereof. The anti-hemorrhagic viral infection agent can be an anti-viral vaccine, an anti-viral antibody, a viral-activated immune cell, or a viral-activated immune serum.

In another embodiment, the immunosuppressant is cyclosporine, tacrolimus, an adrenocortical steroid, azathioprine, mycophenolate, cyclophosphamide, methotrexate, chlorambucil, vincristine, vinblastine, dactinomycin, an antithymocyte globulin, muromonab-CD3 monoclonal antibody, $Rh_0(D)$ immunoglobulin, methoxsalen, or thalidomide.

In other particular embodiments, the homocysteine lowering agent is vitamin $B_6$, vitamin $B_{12}$, or folate.

In yet other embodiments, the anti-neoplasm agent is an anti-angiogenic agent, an alkylating agent, an antimetabolite, a natural product, a platinum coordination complex, an anthracenedione, a substituted urea, a methylhydrazine derivative, an adrenocortical suppressant, a hormone, an antagonist, an oncogene inhibitor, a tumor suppressor gene or protein, an anti-oncogene antibody, or an anti-oncogene antisense oligonucleotide.

The present invention also provides a kit comprising an effective amount of the combination of the present invention, and an instruction means for administering the combination.

Furthermore, the present invention provides a method for reversibly inhibiting activity of a SAH hydrolase in a mammal, comprising administering to a mammal to which such reversible inhibition is needed or desirable, an effective amount of a combination, wherein the combination comprises: a) an effective amount of a compound or a pharmaceutically acceptable salt thereof, having the formula (I):

wherein Z is selected from the group consisting of carbon and nitrogen, R1 and R2 are the same or different, and are selected from the group consisting of hydrogen, hydroxy, alkyl, cycloalkyl, alkenyl, alkoxy, amino, aryl, heteroaryl, and halogen; R3 and R4 are the same or different and are selected from the group consisting of hydrogen, alkyl, acetyl, alkenyl, aryl, and heteroaryl; X is selected from the group consisting of oxygen, nitrogen, and sulfur; and Y is selected from the group consisting of hydrogen, a $C_{1-10}$ alkyl group, alkenyl, vinyl, aryl, and heteroaryl; and b) an effective amount of a compound selected from the group consisting of an anti-hemorrhagic viral infection agent, an immunosuppressant, a homocysteine lowering agent, and an anti-neoplasm agent, thereby reversibly inhibiting said activity of SAH hydrolase in said mammal. In a particular embodiment, the administered combination does not include (4-adenine-9-yl)-2-hydroxybutanoic acid.

The combination can be used with any other pharmaceutical composition to modulate SAH hydrolase activity in a mammal. The combination can also be used in the prevention and treatment of diseases such as hemorrhagic viral infection, autoimmune disease, autograft rejection, neoplasm, and hyperhomocysteineuria, cardiovascular disease, stroke, Alzheimer's disease, diabetes, inflammatory Bowel disease, multiple sclerosis or autoimmune neuritis, as described above. However, it is not intended that the combination be limited to the prevention and uses of particular diseases.

BRIEF DESCRIPTION OF THE SEVERAL VIEWS OF THE DRAWING(S)

DETAILED DESCRIPTION OF THE INVENTION

Figure 1:
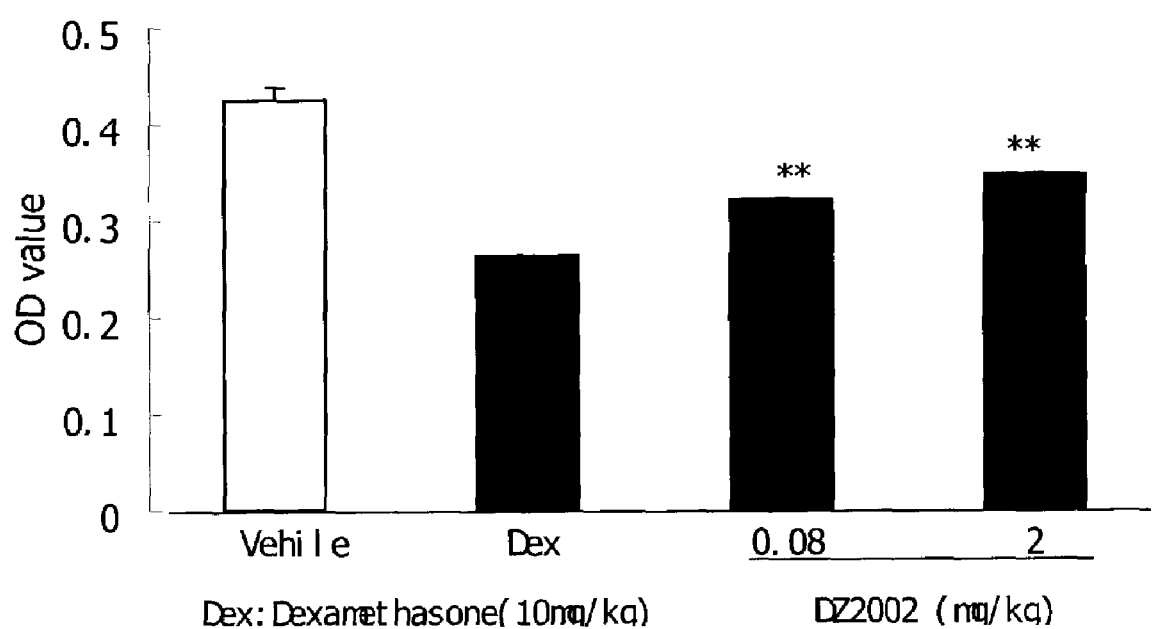
FIG. 1 illustrates effects of DZ2002 on Quantitative hemolysis of Sheep Red Blood Cells (QHS) assay. Data were expressed as means±SD.**: $P<0.01$ compared with control.

For clarity of disclosure, and not by way of limitation, the detailed description of the invention is divided into the subsections that follow.

A. Definitions

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "a" or "an" means "at least one" or "one or more."

As used herein, a "composition" refers to any mixture of two or more products or compounds. It may be a solution, a suspension, liquid, powder, a paste, aqueous, non-aqueous, or any combination thereof.

As used herein, a "combination" refers to any association between two or among more items.

As used herein, "homocysteine" (Hcy) refers to a compound with the following molecular formula: $HSCH_2CH_2CH(NH_2)COOH$. Biologically, Hcy is produced by demethylation of methionine and is an intermediate in the biosynthesis of cysteine from methionine. The term "Hcy" encompasses free Hcy (in the reduced form) and conjugated Hcy (in the oxidized form). Hcy can conjugate with proteins, peptides, itself or other thiols through a disulfide bond.

As used herein, "SAH hydrolase" refers to an enzyme which catalyzes hydrolysis of SAH to adenosine (Ado) and Hcy. The enzyme is an ubiquitous eukaryotic enzyme, which is also found in some prokaryotes. SAH hydrolase also catalyzes the formation of SAH from Ado and Hcy. The co-enzyme of SAH hydrolase is $NAD^+/NADH$. SAH hydrolase may have several catalytic activities. In the hydrolytic direction, the first step involves oxidation of the 3'-hydroxyl group of SAH (3'-oxidative activity) by enzyme-bound $NAD^+(E\text{-}NAD^+)$, followed by β-elimination of L-Hcy to give 3'-keto-4',5'-didehydro-5'-deoxy-Ado. Michael addition of water to the 5'-position to this tightly bound intermediate (5'-hydrolytic activity) affords 3'-keto-Ado, which is then reduced by enzyme-bound NADH (E-NADH) to Ado (3'-reduction activity). It is intended to encompass SAH hydrolase with conservative amino acid substitutions that do not substantially alter its activity.

As used herein, the terms "pharmaceutically acceptable salts" or "pharmaceutically acceptable derivatives" of the compounds of the present invention encompass any salts, esters or derivatives that may be readily prepared by those of skill in this art. Pharmaceutically acceptable salts of the compounds of this invention include, for example, those derived from pharmaceutically acceptable inorganic and organic acids and bases. Salts derived from appropriate bases include, but are not limited to, alkali metal (e.g., sodium), alkaline earth metal (e.g., magnesium), ammonium and $N(C_{1-4} alkyl)_4^+$ salts. Examples of suitable acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, formic, benzoic, malonic, naphthalene-2-sulfonic, and benzenesulfonic acids. Other acids, such as oxalic, while not in themselves pharmaceutically acceptable, may be employed in the preparation of salts useful as intermediates in obtaining the compounds of the invention and their pharmaceutically acceptable acid salts.

As used herein, "biological activity" refers to the in vivo activities of a compound or physiological responses that result upon in vivo administration of a compound, composition, or other mixture. Biological activity, thus, encompasses therapeutic effects and pharmaceutical activity of such compounds, compositions and mixtures. Biological activities may be observed in in vitro systems designed to test or use such activities.

As used herein, "plasma" refers to the fluid, noncellular portion of the blood, distinguished from the serum obtained after coagulation.

As used herein, "serum" refers to the fluid portion of the blood obtained after removal of the fibrin clot and blood cells, distinguished from the plasma in circulating blood.

As used herein, "fluid" refers to any composition that can flow. Fluids thus encompass compositions that are in the form of semi-solids, pastes, solutions, aqueous mixtures, gels, lotions, creams, and other such compositions.

As used herein, the abbreviations for any protective groups, amino acids and other compounds, are in accord with their common usage, recognized abbreviations, or the IUPAC-IUB Commission on Biochemical Nomenclature, unless otherwise indicated (see *Biochemistry* 11: 1726 (1972)).

As used herein, "disease or disorder" refers to a pathological condition in an organism, which is characterizable by identifiable symptoms.

As used herein, the term "a therapeutic agent" refers to any conventional drug or drug therapies which are known to those skilled in the art, including, but not limited to vaccines.

As used herein, "vaccine" refers to any compositions intended for active immunological prophylaxis. A vaccine may be used therapeutically to treat a disease, to prevent development of a disease, or to decrease the severity of a disease either proactively or after infection. Exemplary vaccines include, but are not limited to, preparations of killed microbes of virulent strains, living microbes of attenuated (variant or mutant) strains, or microbial, fungal, plant, protozoa, or metazoa derivatives or products. The term also encompasses protein/peptide and nucleotide based vaccines.

As used herein, the term "therapeutically effective amount" refers to that amount that is sufficient to ameliorate, or in some manner reduce the symptoms associated with the disease. Such amount may be administered as a single dosage or according to a regimen. Repeated administration may be required to achieve the desired amelioration of symptoms.

As used herein, the terms "administration" or "administering" a compound refers to any suitable method of providing a compound of the invention or a pro-drug of a compound of the invention to a subject.

As used herein, the term "treatment" refers to any manner in which the symptoms of a condition, disorder or disease are ameliorated or otherwise beneficially altered. Treatment also encompasses any pharmaceutical use of the compositions herein. Amelioration of symptoms of a particular disorder refers to any lessening of symptoms, whether permanent or temporary, that can be attributed to or associated with administration of the composition.

As used herein, the term "substitute" refers to the replacement of a hydrogen atom in a compound with a substituent group.

As used herein, the term "alkyl" encompasses straight or branched alkyl groups, including alkyl groups that are optionally substituted with one or more substituents. For example, the alkyl group can be optionally substituted with hydroxy, halogen, aryl, alkoxy, acyl, or other substituents known in the art.

As used herein, the term "$K_i$" refers to a numerical measure of the effectiveness of a compound in inhibiting the activity of a target enzyme such as ICE. Lower values to $K_i$ reflect higher effectiveness. The $K_i$ value is derived by fitting experimentally determined rate data to standard enzyme kinetic equations (Segel, Enzyme Kinetics, Wiley-Interscience, 1975).

As used herein, "an anti-neoplastic treatment" refers to any treatment designed to treat the neoplasm, tumor or cancer by lessening or ameliorating its symptoms. Treatments that prevent the occurrence or lessen the severity of neoplasm, tumor or cancer are also contemplated.

As used herein, "neoplasm (neoplasia)" refers to abnormal new growth, and thus means the same as tumor, which may be benign or malignant. Unlike hyperplasia, neoplastic proliferation persists even in the absence of the original stimulus.

As used herein, "an anti-neoplasm agent (used interchangeably with anti-neoplastic agent, anti-tumor or anti-cancer agent)" refers to any agents used in the anti-neoplasm treatment. These include any agents, that when used alone or in combination with other compounds, can alleviate, reduce, ameliorate, prevent, place or maintain in a state of remission clinical symptoms or diagnostic markers associated with neoplasm, tumor or cancer. The anti-neoplasm agent that can be used in the combinations of the present invention include, but are not limited to, anti-angiogenic agents, alkylating agents, antimetabolite, certain natural products, platinum coordination complexes, anthracenediones, substituted ureas, methylhydrazine derivatives, adrenocortical suppressants, certain hormones and antagonists, anti-cancer polysaccharides, and certain herb extracts such as Chinese herb extracts.

As used herein, "tumor suppressor gene" (also referred to as anti-oncogene or cancer susceptibility gene) refers to a gene that encodes a product which normally negatively regulates the cell cycle, and which must be mutated or otherwise inactivated before a cell can proceed to rapid division. Exemplary tumor suppressor genes include, but are not limited to, p16, p21, p53, RB (retinoblastoma), WT-1 (Wilm's tumor), DCC (deleted in colonic carcinoma), NF-1 (neurofibrosarcoma) and APC (adenomatous polypospis coli).

As used herein, "oncogene" refers to a mutated and/or overexpressed version of a normal gene of animal cells (the proto-oncogene) that in a dominant fashion can release the cell from normal restraints on growth. Thus, an oncogene alone, or in concert with other changes, converts a cell into a tumor cell. Exemplary oncogenes include, but are not limited to, abl, erbA, erbB, ets, fes (fps), fgr, fms, fos, hst, int1, int2, jun, hit, B-lym, mas, met, mil (raj), mos, myb, myc, N-myc, neu (ErbB2), ral (mil), Ha-ras, Ki-ras, N-ras, rel, ros, sis, src, ski, trk and yes.

As used herein, "antisense polynucleotides" refer to synthetic sequences of nucleotide bases complementary to mRNA or the sense strand of double stranded DNA. Admixture of sense and antisense polynucleotides under appropriate conditions leads to the binding of the two molecules, or hybridization. When these polynucleotides bind to (hybridize with) mRNA, inhibition of protein synthesis (translation) occurs. When these polynucleotides bind to double stranded DNA, inhibition of RNA synthesis (transcription) occurs. The resulting inhibition of translation and/or transcription leads to an inhibition of the synthesis of the protein encoded by the sense strand.

As used herein, "antibody" includes antibody fragments, such as Fab fragments, which are composed of a light chain and the variable region of a heavy chain.

As used herein, "humanized antibodies" refers to antibodies that are modified to include "human" sequences of amino acids so that administration to a human will not provoke an immune response. Methods for preparing such antibodies are known. For example, the hybridoma that expresses the monoclonal antibody is altered by recombinant DNA techniques to express an antibody in which the amino acid composition of the non-variable regions is based on human antibodies. Computer programs have been designed to identify such regions.

As used herein, "anti-hemorrhagic virus agent" or "antiviral hemorrhagic agent" refer to any agent used in the treatment of hemorrhagic viral infections. These include any agents, alone or in combination with other compounds, that can alleviate, reduce, ameliorate, prevent, or maintain in a place of remission clinical symptoms or diagnostic markers associated with viral hemorrhagic diseases, or disorders. Non-limiting examples of antiviral-hemorrhagic agents include interleukin-1 (IL-1) inhibitors, tumor necrosis factor (TNF) inhibitors, anti-viral vaccines, anti-viral antibodies, viral-activated immune cells, and viral-activated immune sera.

As used herein, "an anti-hemorrhagic virus treatment" refers to any treatment designed to treat hemorrhagic viral infections by lessening or ameliorating the symptoms. Treatments that prevent the infection or lessen its severity are also contemplated.

As used herein, "IL-1 inhibitor" encompasses any substances that prevent or decrease production, post-translational modifications, maturation, or release of IL-1, or any substances that interfere with or decrease the efficacy of the interaction between IL-1 and IL-1 receptor. Preferably, the IL-1 inhibitor is an anti-IL-1 antibody, an anti-IL-1 receptor antibody, an IL-1 receptor antagonist, an IL-1 production inhibitor, an IL-1 receptor production inhibitor, or an IL-1 releasing inhibitor.

As used herein, "tumor necrosis factor" ("TNF") refers to a group of proinflammatory cytokines encoded within the major histocompatibility complex. The TNF family members include TNF α and TNFR (also known as cachectin and lymphotoxin, respectively). Complementary cDNA clones encoding TNA α and TNFR have been isolated. Thus, reference to "TNF" encompasses all proteins encoded by the TNF gene family, including TNF α and TNF, or an equivalent molecule obtained from any other source or that has been prepared synthetically. It is intended to encompass TNF with conservative amino acid substitutions that do not substantially alter its activity.

As used herein, "TNF inhibitor" encompasses any substances that prevent or decrease production, post-translational modifications, maturation, or release of TNF, or any substances that interfere with or decrease the efficacy of the interaction between TNF and TNF receptor. Preferably, the TNF inhibitor is an anti-TNF antibody, an anti-TNF receptor antibody, a TNF receptor antagonist, a TNF production inhibitor, a TNF receptor production inhibitor, or a TNF releasing inhibitor.

B. Reversible Inhibitors of S-Adenosyl-L-Homocysteine Hydrolase

One approach for minimizing mechanism-based cytotoxicity is to optimize the pharmacokinetic profiles of SAH hydrolase inhibitors, such that the inhibitors exhibit reversible inhibiting activity. Pharmacokinetic profiles can be optimized by optimizing $K_{Off}$ values. For example, $K_{Off}$ values are optimized such that they are small enough to produce desired antiviral effects, but large enough to allow adequate recovery of the enzyme activity before the next dose.

Eritadenine Derivatives as Reversible Inhibitors of SAH Hydrolase

The present invention relates to novel inhibitors of S-adenosyl-L-homocysteine compositions that are reversible and potent. For example, the present invention provides compounds with a $K_i$ value of less than 100 nM. In one embodiment, the present invention provides 4(adenine-9-yl)-2-hydroxybutanoic acid, its derivatives, and pharmaceutically acceptable salts thereof, and methods for reversibly inhibiting SAH hydrolase using such compounds.

The reversible inhibitor, 4(adenine-9-yl)-2-hydroxybutanoic acid is synthesized from deoxyl modification of eritadenine at the beta carbon. Eritadenine is a naturally occurring compound and a potent irreversible inhibitor of SAH hydrolase. Deoxyl modification of eritadenine at the beta carbon results in a compound that is a reversible inhibitor, while retaining inhibitory potency. Derivatives of 4(adenine-9-yl)-2-hydroxybutanoic acid can be synthesized using conventional synthetic methods known to one of ordinary skill in the art. (See e.g., Yuan et al., *Adv. Antiviral Drug Des.* 2: 41–88 (1996); Holy et al., *Coll. Czechoslovak Chem. Commun.* 50: 245–279 (1985)).

Examples of 4(adenine-9-yl)-2-hydroxybutanoic acids derivatives include, but are not limited to, base-modified derivatives, and side-chain substituted derivatives. Base modified derivatives are derivatives of 4(adenine-9yl)-2-hydroxybutanoic acids with modifications at the adenyl ring base. The adenyl ring can be modified with various modifying groups at the amino group. The adenyl ring can also be modified with various substituents at the C2 and C8 positions of the adenyl ring.

In one embodiment, the reversible inhibitors of SAH hydrolase have the following formula (I), and pharmaceutically acceptable salts thereof:

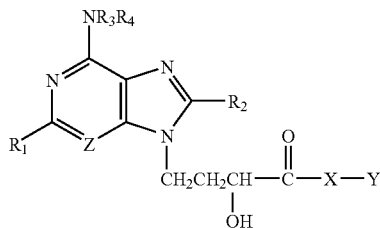

wherein Z is carbon or nitrogen, R1 and R2 are the same or different, and are hydrogen, hydroxy, alkyl, cycloalkyl, alkenyl, alkoxy, amino, aryl, heteroaryl, or halogen; R3 and R4 are the same or different and are hydrogen, alkyl, acetyl, alkenyl, aryl, or heteroaryl; X is oxygen, nitrogen, or sulfur; and Y is hydrogen, a $C_{1-10}$ alkyl group, alkenyl, vinyl, aryl, or heteroaryl.

The different R groups can be optionally substituted with other substituents. These substituents may be halogen, hydroxy, alkoxy, nitro, cyano, carboxylic acid, alkyl, alkenyl, cycloalkyl, thiol, amino, acyl, carboxylate, aryl, carbamate, carboxamide, sulfonamide, a heterocyclic group, or any appropriate substituent known in the art. In a particular embodiment, each R group is hydrogen, or a lower straight chain alkyl such as methyl. In another embodiment, one or more carbon atoms in the alkyl or alkoxy groups may be replaced by one or more heteroatoms.

The amino group may also be substituted once or twice to form a secondary or tertiary amine. Non-limiting examples of substituents include alkyls or an optionally substituted alkyl group; alkene or an optionally substituted alkenyl group; cycloalkyl or an optionally substituted cycloalkyl group; aryl, heterocyclic; aralkyl (e.g. phenyl $C_{1-4}$ alkyl); heteroalkyl such as phenyl, pyridine, phenylmethyl, phenethyl, pyridinylmethyl, pyridinylethyl; and other substituents. The heterocyclic group may be a 5 or 6 membered ring containing 1–4 heteroatoms.

The amino group may be substituted with an optionally substituted $C_{2-4}$ alkanoyl (e.g. acetyl, propionyl, butyryl, isobutyryl etc.); a $C_{1-4}$ alkylsulfonyl (e.g. methanesulfonyl, ethanesulfonyl, etc.); a carbonyl or sulfonyl substituted aromatic or heterocyclic ring (e.g. benzenesulfonyl, benzoyl, pyridinesulfonyl, pyridinecarbonyl etc.).

The CO—X—Y group can be an optionally substituted carboxylate group. Examples of the optionally substituted carboxylate group include, but are not limited to, an optionally substituted alkyl (e.g. $C_{1-10}$ alkyl); an optionally substituted cycloalkyl (e.g. $C_{3-7}$ cycloalkyl); an optionally substituted alkenyl (e.g. $C_{2-10}$ alkenyl); an optionally substituted cycloalkenyl (e.g. $C_{3-7}$ cycloalkenyl); an optionally substituted aryl (e.g. phenyl, naphthyl, $C_{1-4}$ aryl such as benzyl); and other appropriate substituents. Groups such as methoxymethyl, methoxyethyl, and related groups are also encompassed.

Structure-based Drug Design of Novel SAH Hydrolase Inhibitors

It is also an object of the present invention to provide structure-based drug design using the compounds of the present invention as an initial template molecule. Recently, X-ray structures of SAH hydrolase have become available for both "open" and "closed" forms of the enzyme. Using structure-based design, one of ordinary skill in the art can design novel compounds for screening SAH hydrolase inhibitors. The design or selection of candidate compounds can begin with the selection of various moieties which fill binding pockets of the SAH hydrolase. (See e.g., U.S. Pat. No. 5,756,466; Klebe, *J. Mol. Med.* 78: 69–281 (2000); and Maignan et al., *Curr. Top. Med. Chem.* 1: 161–174 (2001)).

There are a number of ways to select moieties to fill individual binding pockets. These include visual inspection of a physical model or computer model of the active site and manual docking of models of selected moieties into various binding pockets. Modeling software that is well known and available in the art can be used. These include, but are not limited to, QUANTA (Molecular Simulations, Inc., Burlington, Mass., 1992); SYBYL (Molecular Modeling Software, Tripos Associates, Inc., St. Louis, Mo., 1992); AMBER (Weiner et al., *J. Am. Chem. Soc.* 6: 765–784 (1984)); CHARMM (Brooks et al., *J. Comp. Chem.* 4: 187–217 (1983)). The modeling step can be followed by energy minimization with standard molecular mechanics forcefields such as CHARMM and AMBER. In addition, there are a number of more specialized computer programs to assist in the process of selecting the binding moieties of this invention. These include, but are not limited to:

1. GRID (Goodford, "A Computational Procedure for Determining Energetically Favorable Binding Sites on Biologically Important Macromolecules,"*J. Med. Chem.* 28: 849–857 (1985)). GRID is available from Oxford University, Oxford, UK.

2. MCSS (Miranker et al., "Functionality Maps of Binding Sites: A Multiple Copy Simultaneous Search Method," in *Proteins: Structure, Function and Genetics*" 11: 29–34 (1991)). MCSS is available from Molecular Simulations, Burlington, Mass.

3. AUTODOCK (Goodsell et al., "Automated Docking of Substrates to Proteins by Simulated Annealing," in PROTEINS: Structure, Function and Genetics 8: 195–202 (1990)). AUTODOCK is available from the Scripps Research Institute, La Jolla, Calif.

4. DOCK (Kuntz et al., "A Geometric Approach to Macromolecule-Ligand Interactions," *J. Mol. Biol.* 161: 269–288 (1982)). DOCK is available from the University of California, San Francisco, Calif.

Once suitable binding moieties have been selected, they can be assembled into a single inhibitor. This assembly may be accomplished by connecting the various moieties to a central scaffold. The assembly process may, for example, be done by visual inspection followed by manual model building, again using software such as QUANTA or SYBYL. A number of other programs may also be used to help select ways to connect the various moieties. These include, but are not limited to:

1. CAVEAT (Bartlett et al., "CAVEAT: A Program to Facilitate the Structure-Derived Design of Biologically Active Molecules," in *Molecular Recognition in Chemical and Biological Problems,* Special Pub., Royal Chem. Soc. 78: 182–196 (1989)). CAVEAT is available from the University of California, Berkeley, Calif.
2. 3D Database systems such as MACCS-3D (MDL Information Systems, San Leandro, Calif.). This area has been recently reviewed by Martin (Martin, "3D Database Searching in Drug Design," *J. Med. Chem.* 35: 2145–2154 (1992)).
3. HOOK (available from Molecular Simulations, Burlington, Mass.)

In addition to the above computer assisted modeling of inhibitor compounds, the inhibitors of this invention may be constructed de novo using either an empty active site or optionally including some portions of a known inhibitor. Such methods are well known in the art. They include, for example:

1. LUDI (Bohm, "The Computer Program LUDI: A New Method for the De Novo Design of Enzyme Inhibitors," *J. Comp. Aid. Molec. Design* 6: 61–78 (1992)). LUDI is available from Biosym Technologies, San Diego, Calif.
2. LEGEND (Nishibata et al., *Tetrahedron,* 47: 8985 (1991)). LEGEND is available from Molecular Simulations, Burlington, Mass.
3. LeapFrog (available from Tripos associates, St. Louis, Mo.).

A number of techniques commonly used for modeling drugs may be employed (see e.g., Cohen et al., *J. Med. Chem.* 33: 883–894 (1990)). Likewise a number of examples in the chemical literature of techniques can be applied to specific drug design projects. (For a review, see, Navia et al., *Curr. Opin. Struc. Biol.* 2: 202–210 (1991)). Using the novel combination of steps of the present invention, the skilled artisan can advantageously avoid time consuming and expensive experimentation to determine enzymatic inhibition activity of particular compounds. The method is also useful in facilitating rational design of SAH hydrolase inhibitors, and therapeutic and prophylactic agents against SAH hydrolase-mediated diseases. Accordingly, the present invention relates to such inhibitors, and methods for identifying or selecting such inhibitors.

A variety of conventional techniques may be used to carry out each of the above evaluations, as well as evaluations necessary in screening a candidate compound for SAH hydrolase inhibiting activity. Generally, these techniques involve determining the location and binding proximity of a given moiety, the occupied space of a bound inhibitor, the deformation energy of binding of a given compound and electrostatic interaction energies. Examples of conventional techniques useful in the above evaluations include, but are not limited to, quantum mechanics, molecular mechanics, molecular dynamics, Monte Carlo sampling, systematic searches and distance geometry methods (Marshall, *Ann. Ref. Pharmacol. Toxicol.* 27: 193 (1987)). Specific computer software has been developed for use in carrying out these methods. Examples of programs designed for such uses include: Gaussian 92 (Gaussian, Inc., Pittsburgh, Pa.); AMBER; QUANTA/CHARMM; and Insight II/Discover (Biosym Technologies Inc., San Diego, Calif.). These programs may be implemented, for instance, using a Silicon Graphics Indigo2 workstation or IBM RISC/6000 workstation model 550. Other hardware systems and software packages will be known and be of evident applicability to those skilled in the art.

Different classes of active SAH hydrolase inhibitors, according to this invention, may interact in similar ways with the various binding pockets of the SAH hydrolase active site. The spatial arrangement of these important groups is often referred to as a pharmacophore. The concept of the pharmacophore has been well described in the literature (See Mayer et al., *J. Comp. Aided Molec. Design* 1: 3–16 (1987); Hopfinger et al. in Concepts and Applications of Molecular Similarity, Johnson and Maggiora (eds.), Wiley (1990))

Different classes of SAH hydrolase inhibitors of this invention may also use different scaffolds or core structures that allow the necessary moieties to be placed in the active site such that the specific interactions necessary for binding may be obtained. These compounds are best defined in terms of their ability to match the pharmacophore, i.e., their structural identity relative to the shape and properties of the active site of SAH hydrolase. Various scaffolds have been described in, for example, Klebe, G., *J. Mol. Med.* 78: 269–281 (2000); Maignan et al., *Curr. Top. Med. Chem.* 1: 161–174 (2001); and U.S. Pat. No. 5,756,466 to Bemis et al.).

S-Adenosyl-L-Homocysteine Hydrolase to be Inhibited

The compounds of the present invention can be used to reversibly inhibit any SAH hydrolase. It is not intended that the present invention be limited to reversibly inhibiting any specific SAH hydrolase.

In one embodiment, the compounds of the present invention can be used to reversibly inhibit SAH hydrolase encoded by nucleic acids containing nucleotide sequences with the following GenBank accession Nos.: AF129871 (*Gossypium hirsutum*); AQ003753 (*Cryptosporidium parvum*); AF105295 (*Alexandrium fundyense*); AA955402 (*Rattus norvegicus*); AA900229 (*Rattus norvegicus*); AA874914 (*Rattus norvegicus*); AA695679 (*Drosophila melanogaster* ovary); AA803942 (*Drosophila melanogaster* ovary; AI187655 (*Manduca sexta* male antennae); U40872 (*Trichomonas vaginalis*); AJ007835 (*Xenopus Laevis*); AF080546 (*Anopheles gambiae*); A1069796 (*T. cruzi* epimastigote); Z97059 (*Arabidopsis thaliana*); AF059581 (*Arabidopsis thaliana*); U82761 (*Homo sapiens*); AA754430 (*Oryza sativa*); D49804 (*Nicotiana tabacum*); D45204 (*Nicotiana tabacum*); X95636 (*D. melanogaster*); T18277 (endosperm *Zea mays*); R75259 (Mouse brain); Z26881 (*C. roseus*); X12523 (*D. discoideum*); X64391 (*Streptomyces fradiae*); W21772 (*Maize Leaf*); AH003443 (*Rattus norvegicus*); U14963 (*Rattus norvegicus*); U14962 (*Rattus norvegicus*); U14961 (*Rattus norvegicus*); U14960 (*Rattus norvegicus*); U14959 (*Rattus norvegicus*); U14937 (*Rattus norvegicus*); U14988 (*Rattus norvegicus*); U14987 (*Rattus norvegicus*); U14986 (*Rattus norvegicus*); U14985 (*Rattus norvegicus*); U14984 (*Rattus norvegicus*); U14983 (*Rattus norvegicus*); U14982 (*Rattus norvegicus*); U14981 (*Rattus norvegicus*); U14980 (*Rattus norvegicus*); U14979 (*Rattus norvegicus*); U14978 (*Rattus norvegicus*); U14977 (*Rattus norvegicus*); U14976 (*Rattus norvegicus*); U14975 (*Rattus norvegicus*); L32836 (*Mus musculus*); L35559 (*Xenopus laevis*); Z19779 (Human foetal Adrenals tissue); L23836 (*Rhodobacter capsulatus*); M15185 (Rat); L11872 (*Triticum aestivum*); M19937 (Slime mold (*D. discoideum*); M80630 (*Rhodobacter capsulatus*).

In another embodiment, the compounds of the present invention can be used to reversibly inhibit SAH hydrolase encoded by nucleic acids containing nucleotide sequences with the GenBank accession Nos. M61831-62832 (see also Coulter-Karis and Hershfield, *Ann. Hum. Genet.*, 53(2): 169–175 (1989)). The compounds of the present invention can also be used to reversibly inhibit SAH hydrolase encoded by nucleic acids containing the nucleotide or amino acid sequences set forth in U.S. Pat. No. 5,854,023.

C. Use as Therapeutic Agents

Reversible inhibition of SAH hydrolase using 4(adenine-9-yl)-2-hydroxybutanoic acid, its derivatives, and pharmaceutically acceptable salts results in significantly reduced cytotoxicity while retaining its therapeutic effects. With its potency and reversibility, the compounds of the present invention can be used as therapeutic agents without the severe toxicity associated with other irreversible inhibitors. The compounds of the present invention are useful as agents demonstrating biological activities related to their ability to inhibit SAH hydrolase. The inhibitory effect on SAH hydrolase can be evaluated using the ratio of the initial rates of SAH hydrolysis in the presence or absence of the inhibitor, or using any methods known to one of ordinary skill in the art. The present invention provides compositions and methods' for the prevention and treatment of diseases such as hemorrhagic viral infection, autoimmune disease, autograft rejection, neoplasm, hyperhomocysteineuria, cardiovascular disease, stroke, Alzheimer's disease, and diabetes. However, it is not intended that the present invention be limited to the prevention and treatment of particular diseases.

1. Hemorrhagic Fever Viruses

The present invention provides compositions and methods for the treatment of viral hemorrhagic fever. The reversible inhibitors of the present invention can serve as a broad-spectrum antiviral agent against all types of viruses causing hemorrhagic fever, including, but not limited to, togavirus, arenavirus, nairovirus, and hantavirus. Broad-spectrum antiviral drugs offer many advantages over narrow-spectrum agents. Because of the difficulty associated with clinical diagnoses of viral pathogens, diagnostic results often arrive too late for the choice of a specific antiviral drug. Immediate action is often necessary to prevent the condition of the patient from worsening, particularly in acute infections where viral chemotherapy must start as soon as the patient presents clinical symptoms.

Inhibitors of S-adenosyl-L-homocysteine (SAH) hydrolase have been reported to be effective in the treatment of Ebola viral infections. The compounds of the present invention can also be used against other hemorrhagic diseases, such as those described in WO 00/64479. Although the mechanism of inhibition is not necessary in practicing the methods of the present invention, the mechanism of action by which the compounds of the present invention inhibit viral replication may be based on inhibition of viral methylation.

2. Autoimmune Diseases and Diseases Associated with Immunosuppression

The present invention contemplates compositions and methods for preventing and treating autoimmune diseases. If a person has an autoimmune disease, the immune system mistakenly attacks the cells, tissues, and organs of a person's own body. As a group, autoimmune diseases afflict millions of Americans. Most autoimmune diseases strike women more often than men. Examples of autoimmune diseases can be found from the National Institute of Health, "Understanding Autoimmune Disease" (http://www.niaid.nih.gov/publications/autoimmune/autoimmune.htm.).

Compounds that modulate SAH hydrolase activity may also be used for the treatment of diseases that are associated with immunosuppression. Immunosuppression can be due to chemotherapy, radiation therapy, enhanced wound healing, enhanced burn treatment, or other drug therapy such as corticosteroid therapy, or a combination of drugs used in the treatment of autoimmune diseases and graft/transplantation rejection. Immunosuppression can also be due to congenital deficiency in receptor function, infectious diseases, parasitic diseases, or other causes.

3. Neoplasm and Cancer

The present invention also contemplates compositions and methods for preventing and treating neoplasms, including, but not limited to neoplasm associated with the adrenal gland, anus, auditory nerve, bile ducts, bladder, bone, brain, breast, bruccal, central nervous system, cervix, colon, ear, endometrium, esophagus, eye, eyelids, fallopian tube, gastrointestinal tract, head, neck, heart, kidney, larynx, liver, lung, mandible, mandibular condyle, maxilla, mouth, nasopharynx, nose, oral cavity, ovary, pancreas, parotid gland, penis, pinna, pituitary, prostate gland, rectum, retina, salivary glands, skin, small intestine, spinal cord, stomach, testes, thyroid, tonsil, urethra, uterus, vagina, vestibulocochlear nerve, vulva, and neoplasm associated with other organs. In particular embodiments, the pharmaceutical compositions of the present invention are useful for the treatment of non-small cell lung cancer, lung cancer, breast cancer, and prostate cancer. The present invention further contemplates compositions and methods for preventing and treating cancers, including, but not limited to those associated with solid tumors, lymphoma, metastatic tumors, glioblastoma tumors, and other carcinomas tumors.

4. Diseases Associated with Increased Homocysteine Levels

Furthermore, it is contemplated that the compounds of the present invention can be used as a plasma homocysteine lowering agent for the prevention and treatment of diseases associated with increased levels of homocysteine. Diseases which have been found to be linked with increased homocysteine levels (i.e., hyperhomocysteinemia) include, but are not limited to cardiovascular diseases, stroke, Alzheimer's disease and diabetes. For example, various studies have shown a relation between hyperhomocysteinemia and coronary heart disease (CHD), peripheral vascular disease, stroke, and venous thrombosis.

The increased risk of stroke from high homocysteine levels also increase the chance of developing Alzheimer's disease. Recent studies have also shown that people with dementia of the Alzheimer's type have elevated levels of homocysteine in their blood. (Selhub et al., "Plasma homocysteine as a risk factor for dementia and Alzheimer's disease," *N. Eng. J. Med.* 46: 476–483 (2002)). Elevated homocysteine has also been linked to complications in diabetes, lupus, and other chronic diseases.

D. Pharmaceutical Compositions

Pharmaceutical compositions of the present invention comprise any of the compounds of the present invention and pharmaceutically acceptable salts thereof, alone or in combination with any pharmaceutically acceptable carriers, adjuvant or vehicle. Acceptable compositions and methods for their administration that can be employed for use in this invention include, but are not limited to those described in U.S. Pat. Nos. 5,736,154; 6,197,801; 5,741,511; 5,886,039; 5,941,868; 6,258,374 and 5,686,102. Examples of pharmaceutically acceptable carriers, adjuvants and vehicles that can be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The formulation, dosage and route of administration can be determined according to methods known in the art (see e.g., *Remington: The Science and Practice of Pharmacy*, Alfonso R. Gennaro (Editor) Mack Publishing Company, April 1997; *Therapeutic Peptides and Proteins: Formulation, Processing, and Delivery Systems*, Banga, 1999; and *Pharmaceutical Formulation Development of peptides and Proteins*, Hovgaard and Frkjr (Ed.), Taylor & Francis, Inc., 2000; *Biopharmaceutical Drug Design and Development*, Wu-Pong and Rojanasakul (Ed.), Humana Press, 1999). In the treatment or prevention of conditions which require SAH hydrolase modulation, an appropriate dosage level will generally be about 0.01 to 500 mg per kg body weight per day. Preferably, the dosage level will be about 0.1 to about 250 mg/kg per day. In more preferred embodiments, the dosage level will range from about 0.1 to about 20 mg/kg per day. The appropriate dosage can be administered in single or multiple dose. It will be understood that the specific dose level and frequency of dosage for any particular subject may be varied and will depend upon a variety of factors, including the activity of the specific compound used, the metabolic stability and length of action of that compound, the age, body weight, general health, sex, diet, mode and time of administration, rate of excretion, drug combination, the severity of the particular condition, and the patient undergoing therapy.

The pharmaceutical compositions of this invention can be administered orally, parenterally, by inhalation spray, topically, rectally, nasally, buccally, vaginally, via an implanted reservoir, or any suitable form of administration. The term parenteral as used herein includes subcutaneous, intracutaneous, intravenous, intramuscular, intra-articular, intrasynovial, intrasternal, intrathecal, intralesional and intracranial injection or infusion techniques. The most suitable route in any given case will depend on the nature and severity of the condition being treated and on the nature of SAH hydrolase inhibitor being used.

The pharmaceutical compositions may be in the form of a sterile injectable preparation, for example, as a sterile injectable aqueous or oleaginous suspension. This suspension may be formulated according to techniques known in the art using suitable dispersing or wetting agents (e.g., Tween 80), and suspending agents. The sterile injectable preparation may also be a sterile injectable solution or suspension in a non-toxic parenterally-acceptable diluent or solvent. For example, the pharmaceutical composition may be a solution in 1,3-butanediol. Other examples of acceptable vehicles and solvents that may be employed in the compositions of the present invention include, but are not limited to, mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of this invention may be orally administered in any orally acceptable dosage form including, but not limited to, capsules, tablets, and aqueous suspensions and solutions. In the case of tablets for oral use, commonly used carriers include, but are not limited to, lactose and corn starch. Lubricating agents, such as magnesium stearate, can also be added. For oral administration in a capsule form, useful diluents include lactose and dried corn starch. When aqueous suspensions are administered orally, the active ingredient is combined with emulsifying and suspending agents. If desired, certain sweetening, flavoring, and coloring agents may be added.

The pharmaceutical compositions of this invention may also be administered in the form of suppositories for rectal administration. These compositions can be prepared by mixing a compound of this invention with a suitable non-irritating excipient. In particular embodiments, the excipient is solid at room temperature but liquid at the rectal temperature. Thus, the excipient will melt in the rectum to release the active components. Such materials include, but are not limited to, cocoa butter, beeswax and polyethylene glycols.

The pharmaceutical compositions of this invention may be administered by nasal aerosol or inhalation. Such compositions are prepared according to techniques well-known in the art of pharmaceutical formulation. For example, such composition may be prepared as solutions in saline, employing benzyl alcohol or other suitable preservatives, absorption promoters to enhance bioavailability, fluorocarbons, and/or other solubilizing or dispersing agents known in the art.

The pharmaceutical compositions of this invention may also be administered topically. For topical application to the skin, the pharmaceutical composition may be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetaryl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches are also included in this invention.

The invention also provides kits for carrying out the therapeutic regimens of the invention. Such kits comprise therapeutically effective amounts of an SAH hydrolase inhibitor, alone or in combination with other agents, in pharmaceutically acceptable form. Preferred pharmaceutical forms include inhibitors in combination with sterile saline, dextrose solution, buffered solution, or other pharmaceutically acceptable sterile fluid. Alternatively, the composition may be lyophilized or desiccated. In this instance, the kit may further comprise a pharmaceutically acceptable solution, preferably sterile, to form a solution for injection purposes. In another embodiment, the kit may further comprise a needle or syringe, preferably packaged in sterile form, for injecting the composition. In other embodiments, the kit further comprises an instruction means for administering the composition to a subject. The instruction means can be a written insert, an audiotape, an audiovisual tape, or any other means of instructing the administration of the composition to a subject.

E. Combinations for Reversibly Inhibiting SAH Hydrolase Activity

The present invention also provides combinations and kits for reversibly inhibiting SAH hydrolase activity. In one embodiment, the present invention provides a combination, comprising an effective amount of a compound having formula I; and an effective amount of an anti-hemorrhagic viral infection agent, an immunosuppressant, a plasma homocysteine lowering agent, or an anti-neoplasm agent. The combination can further comprise a pharmaceutically acceptable carrier or excipient. In yet another aspect, the present invention provides a kit, comprising an effective amount of the combination as described, and an instruction means for administering the combination to a subject.

Any agent that can alleviate or ameliorate clinical symptoms or diagnostic markers associated with viral hemorrhagic diseases can be used in the combination of the present invention. Anti-viral therapeutic agents include, but are not limited to, anti-viral vaccines, anti-viral antibiotics, viral-activated immune cells and viral-activated immune sera. WO 00/64479 describes examples of anti-viral therapeutic agents that can be used in the combination of the present invention. Preferred embodiments are antiviral therapeutic agents that exhibit biological activity against viral hemorrhagic diseases caused by infection of a Bunyaviridaea, a Filoviridae, a Flaviviridae, or an Arenaviridae virus.

Any agent that suppresses the ability of the body's immune system to fight disease can be used in the combination of the present invention. Non-limiting examples of immunosuppressants are cyclosporine, prednisilone, azathioprine, tacrolimus, an adrenocortical steroid, mycophenolate, cyclophosphamide, methotrexate, chlorambucil, vincristine, vinblastine, dactinomycin, an antithymocyte globulin, muromonab-CD3 monoclonal antibody, $Rh_0(D)$ immune globulin, methoxsalen, and thalidomide (See, Goodman & Gilman's The Pharmacological Basis of Therapeutics, (9th Ed.) McGraw-Hill 1996, pages 1294–1304). The immunosuppressant can be taken as a combination of drugs. For example, most people start on a combination of drugs (e.g., cyclosporin, azathioprine, and prednisilone combination) after their transplant. Over a period of time, the doses of each drug and the number of drugs taken may be reduced as the risks of rejection decline.

Any agent that lowers homocysteine levels can be used in the combination of the present invention. Folic acid is known to be an effective homocysteine-lowering agent. Other homocysteine-lowering agents include, but are not limited to, betaine, trimethylglycin, cyanobalamin, and other B-group vitamins. The combination can also include any multi-vitamin and mineral supplement for use in lowering homocysteine. Examples of multivitamin and mineral supplements that can be used in the combinations of the present invention, include, but are not limited to, those described in U.S. Pat. Nos. 6,361,800; 63,003; 6,323,188; 6,274,170; 6,210,686; 6,203,818; and 5,668,173.

Any anti-neoplasm agent can be used in the combination of the present invention. Examples of anti-neoplasm agents that can be used in the compositions and methods of the present invention are described in U.S. patent application No. 2002/044919. In one embodiment, the anti-neoplasm agent used is an anti-angiogenic agent. The anti-angiogenic agent can be an inhibitor of basement membrane degradation, an inhibitor of cell migration, an inhibitor of endothelial cell proliferation, and an inhibitor of three-dimensional organization and establishment of potency. Examples of such anti-angiogenic agent are illustrated in Auerbach and Auerbach, *Pharmacol. Ther.*, 63: 265–311 (1994); O'Reilly, *Investigational New Drugs*, 15: 5–13 (1997); *J. Nat'l Cancer Instit.*, 88: 786–788 (1996); and U.S. Pat. Nos. 5,593, 990; 5,629,327 and 5,712,291. In another embodiment, the anti-neoplasm agent used is an alkylating agent, an antimetabolite, a natural product, a platinum coordination complex, an anthracenedione, a substituted urea, a methylhydrazine derivative, an adrenocortical suppressant, a hormone, and an antagonist.

Other anti-neoplasm agents include, but are not limited to, cytidine, arabinosyladenine (araC), daunomycin, doxorubicin, methotrexate (MTX), fluorinated pyrimidines such as 5-fluorouracil (5-FU), hydroxyurea, 6-mercaptopurine, plant alkaloids such as vincristine (VCR), VP-16 and vinblastine (VLB), alkylating agent, cisplatin, nitrogen Mustard, trisamine, procarbazine, bleomycin, mitomycin C, actinomycin D, or an enzyme such as L-Asparaginase. The antineoplasm agent can also be an oncogene inhibitor such as an anti-oncogene antibody or an anti-oncogene antisense oligonucleotide. In another embodiment, the anti-neoplastic agent is a cellular matrix inhibitor such as an anti-cellular-matrix antibody or an anti-cellular-matrix antisense oligonucleotide. For example, antibodies and antisense oligonucleotides against caveolin-1, decorin, cadherins, catenins, integrins, and other cellular matrix or cellular matrix genes can be used.

In a specific embodiment, the combination further comprises a tumor suppressor gene for combined intratumoral therapy and gene therapy. The gene can be used in the form of naked DNA, complexed DNA, cDNA, plasmid DNA, RNA or other mixtures thereof as components of the gene delivery system. In another embodiment, the tumor suppressor gene is included in a viral vector. Any viral vectors that are suitable for gene therapy can used in the combination. For example, an adenovirus vector (U.S. Pat. No. 5,869, 305), a simian virus vector (U.S. Pat. No. 5,962,274), a conditionally replicating human immunodeficiency viral vector (U.S. Pat. No. 5,888,767), retrovirus, SV40, Herpes simplex viral amplicon vectors and vaccinia virus vectors can be used. In addition, the genes can be delivered in a non-viral vector system such as a liposome wherein the lipid protects the DNA or other biomaterials from oxidation during the coagulation.

F. EXAMPLES

Example 1

Synthesis of Reversible Inhibitors of SAH Hydrolase $^1H$ ($Me_4Si$) NMR spectra were determined with solution in $CDCl_3$ at 400 MHz, $^{13}C$ ($Me_4Si$) at 100.6 MHz unless otherwise noted. Mass spectra (MS) were obtained by atmospheric pressure chemical ionization (APCI) technique. Reagent grade chemicals were used. Solvents were dried by reflux over and distillation from $CaH_2$ under an argon atmosphere, except THF, which was distilled from benzophenone and potassium. TLC was performed on Merck kieselgel 60-$F_{254}$ with MeOH/CHCl$_3$ (1:9) and EtOAc/MeOH (95:5) as developing systems, and products were detected with 254 nm light. Merck kieselgel 60 (230–400 mesh) was used for column chromatography.

Elemental analyses were determined by Galbraith Laboratories, Knoxville, Tenn. Spectral data for isolated compounds were consistent with reported data. (Holy, *Coll. Czech. Chem. Commun.* 43, 3444–3464 (1978); Holy et al., *Coll. Czech. Chem. Commun.* 50: 262–279 (1985); Japanese Patent 69–50781; *Chem. Abstr.* 1972: 514811). The syntheses are schematically shown in Scheme 2.

9-(3,4-O-Isopropylidene-3,4-dihydroxybutyl)adenine (1)

$^1$H NMR δ 1.36 (s, 3, CH$_3$), 1.45 (s, 3, CH$_3$), 2.00–2.05 (m, 1, H2'), 2.22–2.24 (m, 1, H2"), 3.57–3.59 (m, 1, H3'), 4.03–4.06 (m, 2, H4',4"), 4.34–4.43 m, 2, H1', 1"), 5.76 (br s, 2, NH$_2$), 7.86 (s, 1, H8), 8.38 (s, 1, H2); MS (APCI) m/z 264 (100, MH$^+$).

9-(3,4-Dihydroxybutyl)adenine (2)

A solution of 1 (110 mg, 0.18 mmol) in CF$_3$COOH/H$_2$O (9:1) (5 ml) was stirred for 20 min at ~0° C. Volatiles were evaporated, coevaporated with toluene (3×) and EtOH (2×) to give 2 (73 mg, 78%) after crystallization from EtOH with spectra data as reported.

9-(4-O-t-Butyldimethylsilyl-3,4-dihydroxybutyl)adenine (3)

TBDMS-Cl (186 mg, 1.23 mmol) and imidazole (168 mg, 2.46 mmol) were added to a stirred solution of 2 (250 mg, 1.12 mmol) in dry DMF (8 mL). The mixture was stirred at ambient temperature for 5 h, then reaction mixture was partitioned between EtOAc/NH$_4$Cl/H$_2$O. The water layer was extracted with next portion of EtOAc. The combined organic phase was washed (brine), dried (Na$_2$SO$_4$), evaporated and the residue was column chromographed (CHCl$_3$/MeOH; 97: 3) to give 3 (234 mg, 62%): $^1$H NMR δ 0.04 (s, 6, 2×CH$_3$), 0.88 (s, 9, t-Bu), 1.81–1.89 (m, 1, H2'), 2.03–2.11 (m, 1, H2") 3.50–3.52 (m, 2, H4',4"), 3.58–3.59 (m, 1, H3'), 4.32–4.45 (m, 2, H1',1"), 6.10 (br s, 2, NH$_2$), 7.87 (s, 1, H8), 8.36 (s, 1, H2); $^{13}$C NMR δ −5.0 & −4.9 (2×CH$_3$) 18.7 (t-Bu), 26.3 (t-Bu), 33.7 (C2'), 40.9 (C 1'), 67.4 (C4'), 68.4 (C3'), 119.9 (C5), 141.4 (C8), 150.5 (C4), 153.1 (C2), 155.8 (C6); MS (APCI) m/z 338 (100, MH$^+$). Anal. Calcd for C$_{15}$H$_{27}$N$_5$O$_2$Si (337.50): C, 53.38; H, 8.06; N, 20.75.

9-[4-O-t-Butyldimethylsilyl-3-O-(1-ethoxyethyl-3,4-dihydroxybutyl] adenine (4)

Ethyl vinyl ether (214 mg, 0.28 mL, 2.96 mmol) and pyridinium p-toluenesulfonate (15 mg, mmol) were added to a solution of 3 (250 mg, 0.74 mmol) in dry CH$_2$Cl$_2$ (30 mL), and the mixture was stirred at ambient temperature under N$_2$ until no starting material was detected by TLC (usually 5–6 days). Then reaction mixture was washed with water, dried (Na$_2$SO$_4$), and was evaporated. Column chromatography (EtOAc/MeOH; 97: 3) gave 4 (160 mg, 53%) as ~1:1 mixture of diastereoisomers: $^1$H NMR δ 0.04 (s, 6,2×CH$_3$), 0.88 (s, 9, t-Bu), 1.18–1.34 (complex m, 6, 2×CH$_3$), 2.05–2.21 (m, 2, H2',2"), 3.50–3.63 (complex m, 4, H4',4", CH$_2$), 3.70–3.82 (m, 1, H3'), 4.31–4.40 (m, 2, H1', 1"), 4.72–4.78 & 4.88–4.93 (2×m, 1, CH), 5.99 & 6.06 (2×br s, 2, NH$_2$), 7.86 & 8.04 (2×s, 1, H8), 8.37 (s, 1, H2); $^3$C NMR δ 6–5.1(2×CH$_3$), 15.7 & 15.9 (CH$_3$), 18.6 (t-Bu), 20.7 & 21.0 (CH$_3$), 26.2 (t-Bu), 32.5 & 32.7 (C2'), 41.0 & 41.1 (C1'), 61.0 & 62.1 (CH$_2$), 65.5 & 66.1 (C4'), 73.6 & 74.8 (C3'), 100.2 & 100.5 (CH), 119.9 (C5), 141.1 & 142.2 (C8), 150.5 (C4), 152.1 & 152.5 (C2), 155.3 (C6); MS (APCI) m/z 410 (100, MH$^+$). Anal. Calcd for C$_{19}$H$_{35}$N$_5$O$_3$Si (409.60): C, 55.71; H, 8.61; N, 17.10.

9-[3-O-(1-Ethoxyethyl)-3,4-dihydroxybutyl] adenine (5)—Procedure A

TBAF/THF (0.88 mL, 1M) was added to a solution of 4 (180 mg, 0.44 mmol) in dry THF (6 mL) and the mixture was stirred at ambient temperature for 20 min. Volatiles were evaporated and the residue was column chromatographed (EtOAc/MeOH; 78:12) to give 5 (120 mg, 92%) as 1:1 mixture of diastereoisomers: $^1$H NMR δ 1.21–1.25 (complex m, 3, CH$_3$), 1.35 & 1.39 (d, J=5.3 Hz, 3, CH$_3$), 2.05–2.25 (m, 2, H2',2"), 3.53–3.82 (complex m, 5, H3',4',4", CH$_2$), 4.32–4.39 (m, 2, H1',1"), 4.69 & 4.88–4.87 (q, J=5.3 Hz, 1, CH), 5.88 & 5.92 (2×br s, 2, NH$_2$), 7.82 & 7.94 (2×s, 1, H8), 8.36 (s, 1, H2); $^{13}$C NMR δ 15.5 & 15.7 (CH$_3$), 20.4 & 20.6 (CH$_3$), 32.5 & 32.7 (C2'), 40.0 & 41.1 (C1'), 60.9 & 62.4 (CH$_2$), 64.9 & 65.9 (C4'), 73.2 & 78.9 (C3'), 99.6 & 101.5 (CH), 119.7 (C5), 140.8 & 141.5 (C8), 150.5 (C4), 152.8 & 153.1 (C2), 155.6 & 155.7 (C6); MS (APCI) m/z 296 (100, MH$^+$). Anal. Calcd for C$_{13}$H$_{21}$N$_5$O$_3$ (295.34): C, 52.87; H, 7.17; N, 23.71.

Methyl 4-(Adenin-9-yl)-2-hydroxybutanoate (6)—Procedure B

To a suspension of 5 (90 mg, 0.31 mmol) in CH$_3$CN/CCl$_4$/H$_2$O (1:1:1.5; 1.5 mL), NaHCO$_3$ (161 mg, 0.88 mmol), NaIO$_4$ (353 mg, 1.65 mmol) and RuCl$_3$ (trace) were added. The mixture was stirred at ambient temperature for 48 h until no starting material was detected on TLC. Then water (5 mL) and CHCl$_3$ (4 mL) were added, the two layers were separated and water phase was washed with CHCl$_3$ (3 mL). The aqueous layer was acidified with HCl to pH ~4 and applied on a column of Dowex 50W×2(H$^+$). Column was washed with 200 mL of water then product was eluted with 2.5% NH$_4$OH/H$_2$O. The combined UV-absorbing ammonia eluate was evaporated and coevaporated with MeOH (2×). The residue was dissolved in MeOH (5 mL) and a solution of CH$_2$N$_2$ in diethyl ether was added until yellow color of diazomethane was maintained during several minutes. The solution was concentrated and column chromatographed (CHCl$_3$/MeOH; 95:5) to give 6 (31 mg, 41%) as a white solid with data identical as reported. To avoid formation of by-product 6' it is imported to keep desired amount of NaHCO$_3$ in reaction mixture.

4-(Adenin-9-yl)-2-hydroxybutanoic acid (7)—Procedure C

NaOH/H$_2$O (1 mL. 0.1 M) was added to a solution of 6 (10 mg, 0.04 mmol) in MeOH/H$_2$O (2.0 mL). The mixture was stirred at ambient temperature for 6 h until no starting material was detected on TLC. Then reaction mixture was acidified with HCl to pH ~4 and applied on a column of Dowex 50W×2(H$^+$). Column was washed with water (100 mL) and then product was eluted with 2.5% NH$_4$OH. The combined UV- absorbing ammonia eluate was evaporated to give 7 as a ammonium salt (7.6 mg, 75%) with data as reported.

9-(3,4-O-Di-t-Butyldimethylsilyl-3,4-dihydroxybutyl)adenine (8)

TBDMS-Cl (593 mg, 3.92 mmol) and imidazole (534 mg, 7.85 mmol) were added to a stirred solution of 2 (350 mg, 1.57 mmol) in dry DMF (8 mL), and the mixture was stirred at ambient temperature overnight. Then reaction mixture was partitioned between EtOAc/NH$_4$Cl/H$_2$O. The water layer was extracted with EtOAc. The combined organic phase was washed (brine), dried (Na$_2$SO$_4$), and evaporated. Column chromatography (CHCl$_3$ → 3% MeOH/CHCl$_3$) gave 8 (610 mg, 86%): $^1$H NMR δ 0.04 (s, 6, 2×CH$_3$), 0.09 (s, 6, 2×CH$_3$), 0.88 (s, 9, t-Bu), 0.92 (s, 9, t-Bu), 2.02–2.07 (m, 1, H2'), 2.21–2.26 (m, 1, H2"), 3.46 (dd, J=6.8, 10.0 Hz, 1 H4'), 3.59 (dd, J=5.2, 10.0 Hz, 1, H4"), 3.78–3.81 (m, 1, H3'), 4.32–4.45 (m, 2, H1',1"), 5.96 (br s, 2, NH$_2$), 7.84 (s 1, H8), 8.42 (s, 1, H2); MS (APCI) m/z 452 (100, MH$^+$). Anal. Calcd for C$_{21}$ H$_{41}$ N$_5$O$_2$Si$_2$ (451.76): C, 55.83; H, 9.15; N, 15.50.

9-(3-O-t-Butyldimethylsilyl-3,4-dihydroxybutyl)adenine (9)

Compound 8 (400 mg, 0.887 mmol) was added to a solution of CH$_3$CO$_2$H/H$_2$O/THF (13:7:3; 8 mL) and the mixture was stirred at ambient temperature until more polar spot of compound 2 starting to appear on TLC. Then reaction mixture was partitioned (EtOAc//NaHCO$_3$/H$_2$O) and the aqueous layer was extracted with next portion of EtOAc. The combined organic phase was washed (NaHCO$_3$, brine), dried (Na$_2$SO$_4$), evaporated and column chromatographed (CHCl$_3$ →4% MeOH/CHCl$_3$) to give recovered 8 (140 mg, 35%) and 9 (155 mg, 52%): $^1$HNMR δ 0.04 (s, 6, 2×CH$_3$), 0.88 (s, 9, t-Bu), 2.16–2.19 (m, 2, H2',2"), 3.61 (dd, J=4.5, 11.4 Hz, 1, H4"), 3.65 (dd, J=5.2, 11.4 Hz, 1, H4"), 3.88 (q, J=5.2 Hz, 1, H3'), 4.26–4.36 (m, 2, H1',1"), 6.17 (br s, 2, NH$_2$), 7.80 (s, 1, H8), 8.29 (s, 1, H2); $^{13}$C NMR δ −4.4 & 4.1 (CH$_3$), 18.5 (t-Bu), 26.2 (t-Bu), 34.5 (C2'), 40.8 (C1'), 65.5 (C4'), 70.6 (C3'), 119.8 (C5), 140.7 (C8), 150.4 (C4), 153.0 (C2), 155.5 (C6); MS (APCI) m/z 338 (100, MH$^+$). Anal. Calcd. for C$_{15}$H$_{27}$N$_5$O$_2$Si (337.50): C, 53.38; H, 8.06; N, 20.75.

Methyl 3-(Adenin-9-yl)propionate (6')

Treatment of 9 (50 mg, 0.148 mmol) by procedure B (column chromatography: CHCl$_3$/MeOH 97:3) gave 6' (9 mg, 27%) with data as reported.

3-(Adenin-9-yl)propionic acid (7')

Treatment of 6' (10 mg, 0.045 mmol) by procedure C (column chromatography: CHCl$_3$/MeOH 97:3) gave 6' (7.3 mg, 78%) with data as reported.

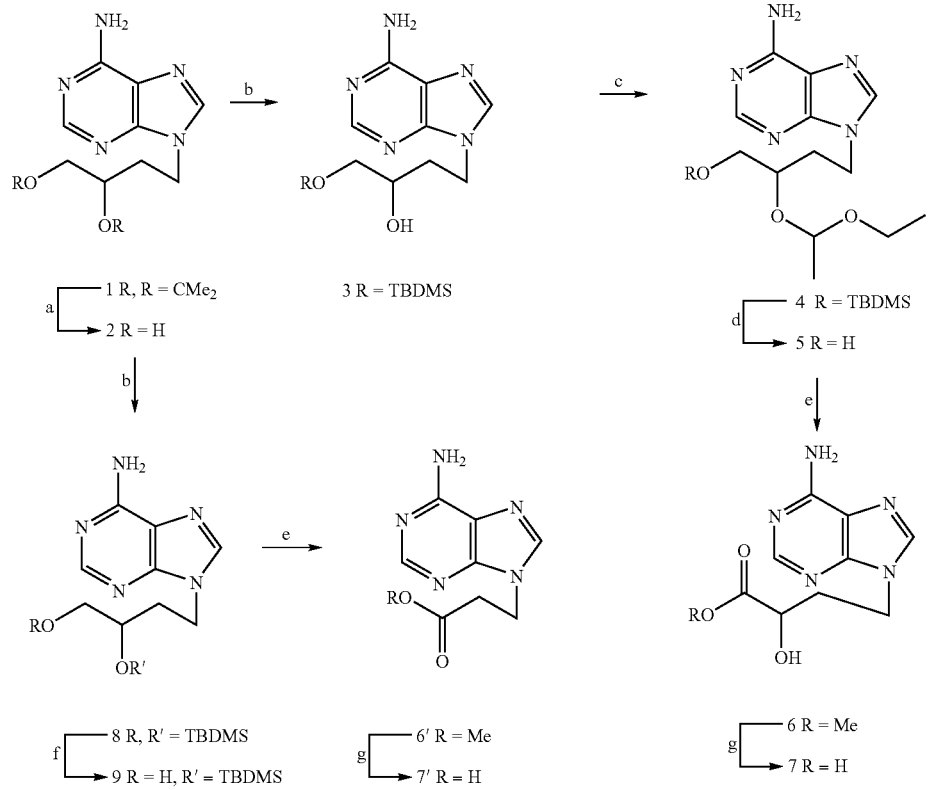

Scheme 2

$^a$(a) CF$_3$COOH/H$_2$O; (b) TBDMSCl/imidazole/DMF; (c) ethyl vinyl ether/CH$_2$Cl$_2$/(p)CH$_3$C$_6$H$_4$SO$_3$H•C$_5$H$_{10}$N; (d) TBAF/THF; (e) (i) NaIO$_4$/NaHCO$_3$/RuCl$_3$/CH$_3$CN/CCl$_4$/H$_2$O, (ii) CH$_2$N$_2$/MeOH; (f) CH$_3$CO$_2$H/H$_2$O/THF; (g) NaOH/H$_2$O/MeOH.

Example 2

DZ2002 Mediates Immunosuppressive Effects

Materials and Methods

Reagents

AdoHcy hydrolase inhibitors DZ2002 was synthesized at Diazyme Laboratories. Con A (Concanavalin A), LPS (*Escherichia coli* 055:B5) and Sac (Staphylococcus aureus Cowan strain 1) were obtained from Pansorbin® cells, Biosciences, inc.(La Jolla., Calif. 92039, USA). RPMI 1640 and fetal bovine serum (FBS) were obtained from GIBCO. Purified rat anti-mouse IL-10, IL-12p70, IL-12p40, IFN-γ and biotinylated anti-mouse IL-10, IL-12p70, IL-12p40, IFN-γ, FITC-anti-mouse-CD11b (Mac-1), Phycorythrin (PE)-anti-mouse I-Ad, PE-anti-human-CD14, PE- anti-human-ABC, PE-anti -human-DR, PE-anti-human-CD80 and PE-anti-human-CD86 were Pharmingen products. Thioglycollate (TG) is available from Sigma-Aldrich.

Animal

Inbred BALB/C mice, 6~8 weeks of age, were provided by Shanghai Experimental Animal Center of Chinese Academy of Sciences with Certificate No. 99-003. The mice were housed in specific pathogen-free (SPF) conditions with room temperature of 24±2° C., 12 hr light/dark cycle, and provided with sterile food and water ad libitum.

Cells

Spleens from Balb/c mice were aseptically removed, pooled, and single cell suspensions prepared in PBS. Erythrocytes were lysed by treatment with Tris-buffered ammonium chloride (0.155 M $NH_4CL$, 0.0165 M Tris, PH 7.2). Mononuclear cells were washed with PBS and resuspended in RPMI-1640 media supplemented with benzylpenicillin 100000 $U·L^{-1}$, and streptomycin 100 $mg·L^{-1}$. The cell viability and concentration were determined by trypan blue exclusion.

Peritoneal exudate cells were induced in BALB/C mice by an intraperitoneal injection of 0.5 ml of 3% TG. After 4 days, the peritoneal exudates cells were harvested by sterile lavage.

THP-1 (American Type Culture Collection, Manassas, Va.) is a human monocytic leukemia. THP-1 cells were maintained in suspension culture in RPMI1640 medium supplemented with 10% FBS. Cultures were maintained at 37° C. in a humidified atmosphere of 5% $CO_2$ in air and were subculture at 1/10 dilution every 5–6 days.

[$^3$H]-thymidine Incorporation to the Splenic Lymphocytes

Mouse splenic lymphocytes were cultured in vitro in RPMI1640 supplemented with 10% FBS. Cells were incubated in a 96-well plate at $1 \times 10^5$ cells/200 μl/well in a humidified $CO_2$ incubator at 37° C. for 48 hours with 5 μg/ml of Con A or 10 μg/ml LPS in the presence or absence of various concentrations of DZ2002. After 40 hour incubation, cells were pulsed with 0.5 μCi/well of [$^3$H]-thymidine and cultured for another 8 hours. The cells were then harvested onto glass fiber filters and the incorporated radioactivity was counted using a Beta Scintillator (MicroBeta Trilux, PerkinElmer Life Sciences).

MTT Assay of the Splenic Lymphocytes

Cytotoxicity was assessed with MTT assay. Mouse splenic lymphocytes were incubated in a 96-well plate at $9 \times 10^4$ cells/180 μl/well in a humidified $CO_2$ incubator at 37° C. for 48 hours in the presence or absence of various concentrations of DZ2002. Fifteen (15) μl of 5 mg/ml of MTT was pulsed 4 h prior to end of the culture (total 190 μl), and then 80 μl solvent (10% SDS, 50% N,N-dimethy formamide, PH7.2) was added. Incubate for 7 h and read $OD_{590}$ at a microplate reader (Bio-rad Model 550 Japan).

Cytokine Production

Murine splenic mononuclear cells ($5 \times 10^6$) were cultured in 24-well plates in a volume of 2 ml/well in the presence of Sac (1:10000), ConA (5 ug/ml) or LPS (10 ug/ml) in the presence or absence of various concentrations of DZ2002. After 24 h, cell-free supernatant was collected and frozen at −20° C. The concentrations of IL-12p40, IL-12p70, IL-10 and TNF-α were determined in an ELISA specific for murine cytokines.

Murine peritoneal exudate cells ($6.25 \times 10^5$) were cultured in 24-well plates in a volume of 1 ml/well for 2 hours. In adherent cells were washed by ice cold RPMI 1640 and adherent cells were culture in a volume of 2 ml/well in the presence of IFN-γ (2.5 ng/ml) and LPS (1 μg/ml) in the presence or absence of various concentrations of DZ2002. After 24 h, cell-free supernatant was collected and frozen at −20° C. The concentrations of IL-12p40, IL-12p70, IL-10 and TNF-α were determined by ELISA.

THP-1 cells ($6 \times 10^5$) were cultured in 24-well plates in a volume of 2 ml/well in the presence of 1.2% and in the presence or absence of various concentrations of DZ2002. After 24 h, IFN-γ(500 U/ml) was added and another 16 h later, LPS (1 μg/ml) was added. Cell-free supernatant was collected after 24 h and frozen at −20° C. The concentrations of IL-12p40, IL-12p70, IL-10 and TNF-α were determined for ELISA.

Quantitative Hemolysis of Sheep Red Blood Cells (QHS) Assay

Female Babl/c mice were immunized by intraperitoneal injection with 0.2 ml of 16.7% of SRBC on day 4. Vehicle, Dexamethasone and DZ2002 were administered on each group (n=6) by intraperitoneal injection on 7 consecutive days of 1–7. On day8, mice were sacrificed and made a mixed suspension of spleen cells of $2 \times 06$ cells/ml. 1 ml of cell suspension was incubated with 1 ml of 0.5% SRBC and 1 ml of 1:10 dilution of guinea pig complement for 1 h at 37° C., then centrifuged (3 min, 3000 g) and determined the supernatant hemolysis at 413 nm, according to Simpson et al, J. Immunol. Methods., 21(1–2):159–65.(1978) with some modifications. Each group was triplicated.

Mixed Lymphocyte Reaction (MLR) Proliferation Assay.

Balb/c mouse spleen cells were prepared in $10^7$ cells/ml suspension, cultured 2 h with 50 μg/ml of mitomycin. Then cells were washed and cultured together with fresh C57/B6 mice splenocytes equally in a final concentration of $1.0 \times 10^6$ cells/ml in the presence or absence of various concentrations of DZ2002. After 48 hour incubation, cells were pulsed with 0.5 μCi/well of [$^3$H]-thymidine and cultured for another 24 hours. The cells were then harvested onto glass fiber filters and the incorporated radioactivity was counted using a Beta Scintillator (MicroBeta Trilux, PerkinElmer Life Sciences).

DNFB-induced Delayed Type Hypersensitivity (DTH) Response

Female Balb/c mice were sensitized with 20 μl of 0.6% DNFB dissolved in acetone-olive oil (4:1) on each hind foot on day0 and 1. On day 7 mice were challenged with 10 μl of 0.5% DNFB on both sides of left ear, methods according to Phanuphak (1974) with some modifications. Vehicle, CsA, and DZ2002 (1, 3, 10 mg/kg) were administrated on each group (n=10) by intraperitoneal injection on 1 hour before and 12 hours, 24 hours after the challenge. Ear swelling was expressed as difference between the weight of the left and right ear patches made by a specific 8-mm punch 30 h after the challenge.

Flow Cytometry

Murine peritoneal exudate cells or THP-1 cells were washed in cold PBS (staining buffer, containing 0.1% $NaN_3$, 1% FBS, PH 7.2). Cells were resuspended at $2.0 \times 10^7$/ml in cold staining buffer. Optimal concentrations of each fluorochrome-labeled antibody were added to 50 μL cells. Fc receptors were blocked using 10 μL normal mouse serum. Cells were incubated in the dark at 4° C. for 30 min, washed twice with 2.0 mL staining buffer and resuspended in 0.5 mL of PBS, PH 7.2. Cells were stored in the dark at 4° C. and analyzed on a FACScan flow cytometer (Becton Dickinson, San Jose, Calif.). Data were analyzed by means of CellQuest™ Software (Becton Dickinson, San Jose, Calif.).

Statistical Analysis

Results were expressed as x±s, independent two-tailed t-test was performed and P values less than 0.05 were considered to be significant. Each experiment was repeated at least three times.

Results

Inhibition of [$^3$H]-Thymidine Incorporation to the Splenic Lymphocytes by AdoHcy Hydrolase Inhibitors After 48 h of culture, DZ2002 (0.1–10 μmol·L$^{-1}$) have no effects on the lymphocytes proliferation induced by ConA. DZ2002 (10 μmol·L$^{-1}$) inhibited lymphocytes proliferation induced by LPS.

Effect of DZ2002 on IL-10, IL-12P40 and IL-12P70 Production from Sac Stimulated Murine Splenocytes Sac stimulation induced marked increasing of IL-10, IL-12P40 and IFN-γ production from murine splenocytes compared with resting splenocytes. DZ2002 (μmol·L$^{-1}$) dose dependently inhibited IL-12P40, IL-12P70 and TNF-α release, but have no effect on IL-10 production from Sac stimulated splenocytes. (data not shown).

Figure 3:
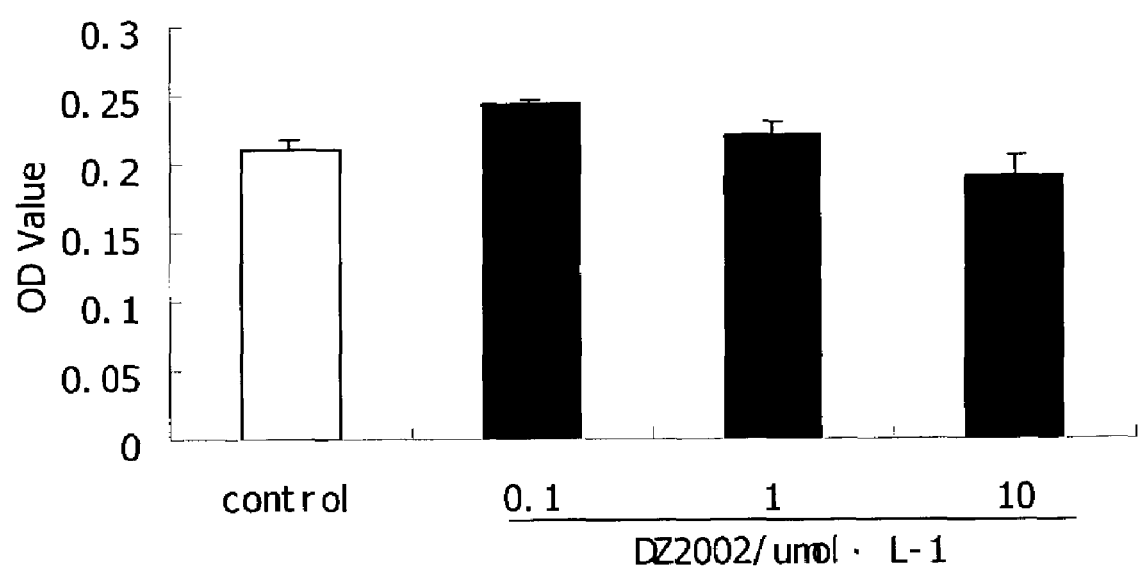
FIG. 3 illustrates that DZ2002 have no cytotoxicity in spleen cell.
Figure 4:
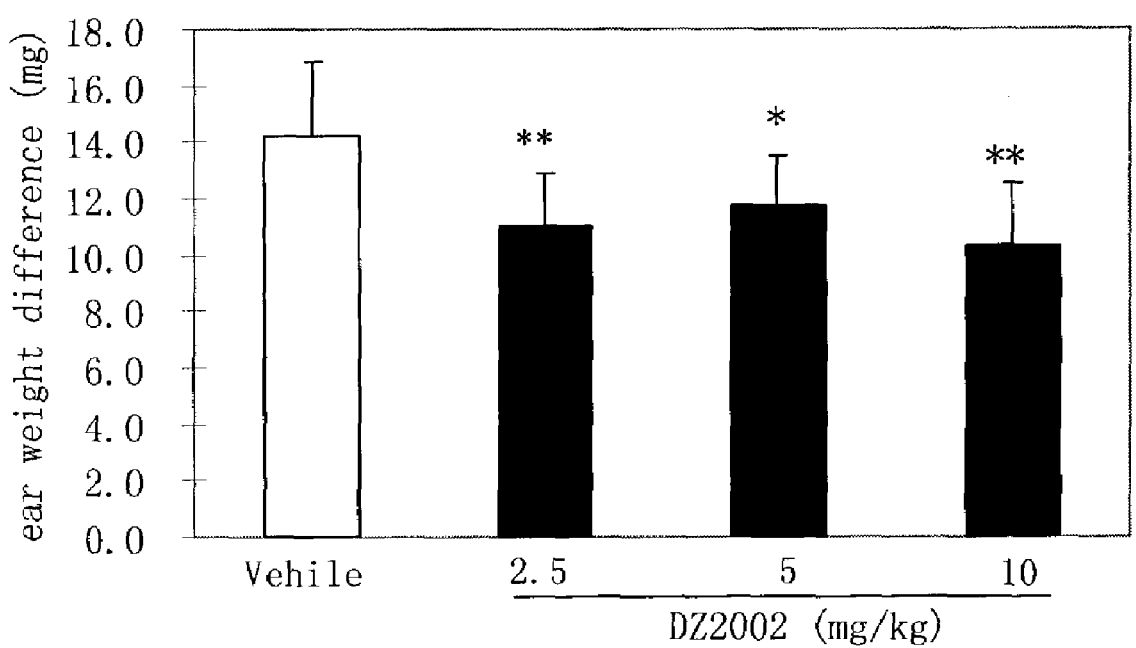
FIG. 4 illustrates effects of DZ2002 on DTH ear swelling in Balb/c mice.

Effects of DZ2002 On Quantitative Hemolysis of Sheep Red Blood Cells (QHS) Assay Quantitative hemolysis of SRBC is a model of primary antibody production in response to antigenic stimulation. As FIG. 3 shows, consecutively 7-day intraperitoneal injection of DZ2002 inhibited 24.5 and 18.4% of QHS at doses of 0.08 and 2 mg/kg respectively, compared with 38.1% of that of 5 mg/kg Dethamethasone (p<0.05 for All experiment groups compared with Vehicle control group) (FIG. 1).

DZ2002 Suppress T Cell Proliferation in Mixed Lymphocyte Reaction

Figure 2:
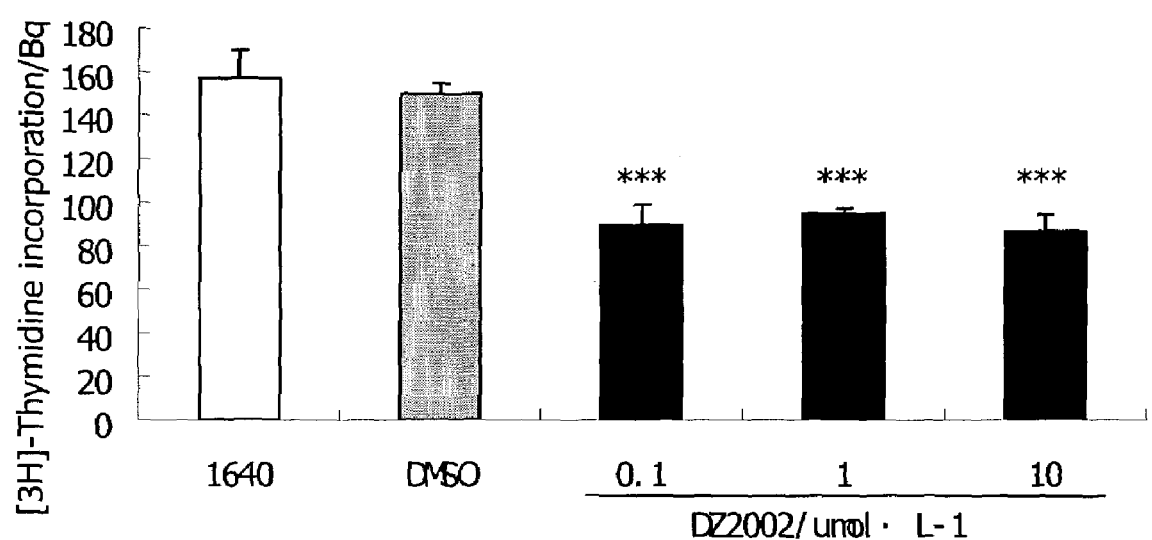
FIG. 2 illustrates that DZ2002 suppresses T cell proliferation in mixed lymphocyte reaction. Data were expressed as means±SD.***: $P<0.001$ compared with control.

Mitomycin-treated Balb/c (H-2$^d$) spleen cell were applied as allogeneic stimulator to C57BL/6(H-2$^b$) spleen cells proliferation. DZ2002 had a strong suppression to MLR with 40.2, 36.9 and 42.3% at doses of 0.1, 1 and 10 μmol/L respectively for 3-day culture. (FIG. 2).

DZ2002 have no Cytotoxicity in Spleen Cell

In two days of culture, 0.1–10 mmol/L DZ2002 showed no cytotoxicity to spleen cells. The OD values of cells incubated with DZ2002 have no difference with that of the control. (FIG. 3).

DZ2002 Reversed the Suppression of Mouse DTH Response Induced by DNFB

Nine mice were prepared for each group. Mice were sensitized with 0.5% DNFB solution (20 ul ) in absolute acetone/olive oil (4:1) on each hind foot on day 0 and 1. Five days after initial sensitization, mice were challenged with 0.2% DNFB (10 ul) on both sides of left ear under light Metofane anesthesia. The right ear was treated with vehicle alone. DZ2002 were orally administered to the mice 1 h before DNFB challenge. The degree of ear swelling was measured 24 h after challenge using a ear puncher and an analytic balance to measure the weight (mg). Results were expressed as the difference between the weight of the left and the right ear. Spleens were taken from four mice in each group after the measurement of the ear swelling and frozen until analysis Effects of DZ2002 on the Expression of MHC-II on Resident and TG Induced Peritoneal Cells MHC-II expression by peritoneal macrophages was assessed following a 48-h incubation with media alone or with IFN-γ at 100 U/ml. Cells incubated with IFN-γ in the present of 0.1 and 1 μmol/L DZ2002 enhance the levels of MHC-II expression of resident peritoneal cells and 10 μmol/L DZ2002 reduce the levels of MHC-II expression. (data not shown) As reflected in the TG induced peritoneal cells, 1 and 10 μmol/L DZ2002 decrease the Mac-1$^+$ percentage when incubate with media alone. And the level of MHC-II expression of cells incubated with IFN-γ was dose-dependently decreased in the presence of 0.1–10 μmol/L DZ2002. (data not shown).

Figure 5:
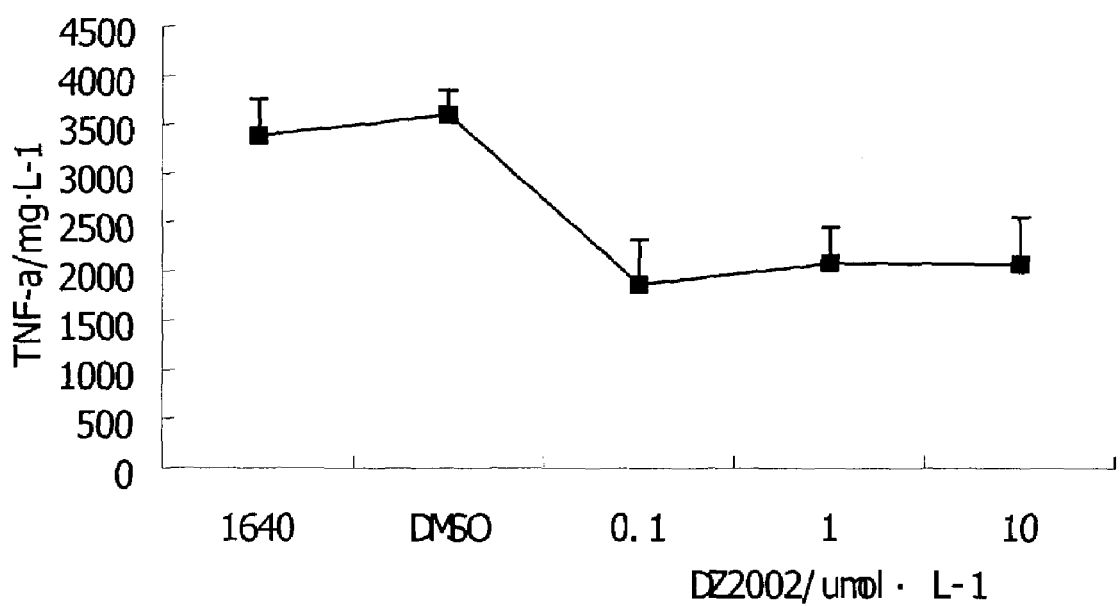
FIG. 5 illustrates effects of DZ2002 on TNF-α production from TG induced peritoneal cells.

Effect of DZ2002 on IL-10, IL-12P40 and TNF-α Production from TG Induced Peritoneal Cells Cytokines produced by peritoneal macrophages were assessed following a 24-h incubation with IFN-γ at 25 U/ml and LPS at 1 μg/ml. Resident peritoneal cells produce low levers of cytokines except for some IL-10 with incubated with IFN-γ and LPS (data not shown). As for TG induced peritoneal macrophages, DZ2002 inhibited IL-12P40 and TNF-α release, but have no effect on IL-10 production in the dose of 0.1–10 μmol/L (FIG. 5).

DZ2002 Inhibits Expression of MHC-II, CD80 and CD86 on THP-1 Cells

Figure 6:
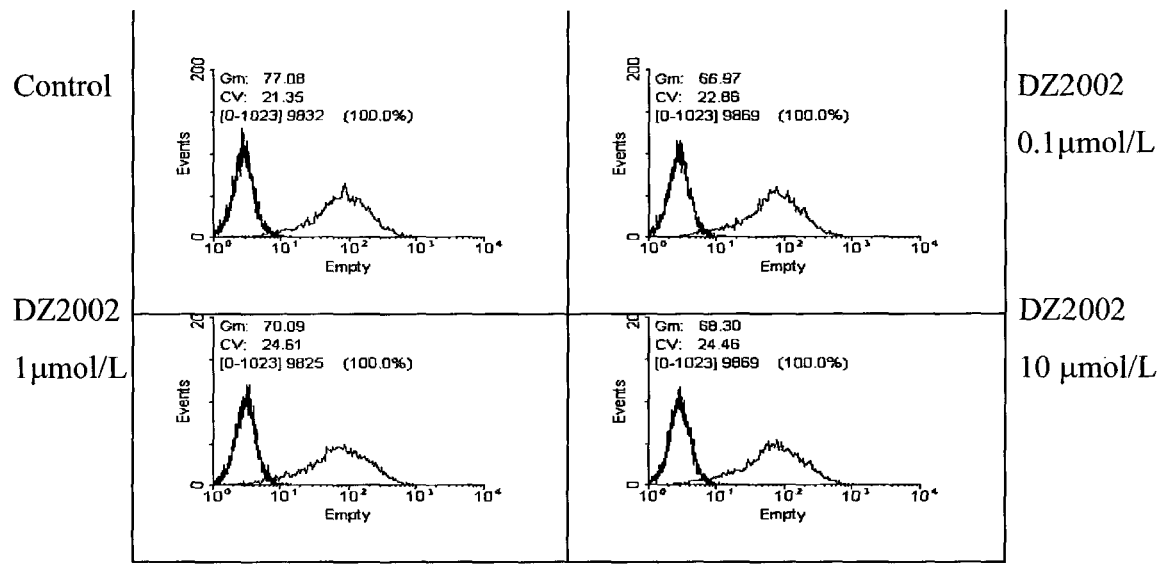
FIG. 6A illustrates effects of DZ2002 on the expression of MHC-II on THP-1 cells.
FIG. 6B illustrates effects of DZ2002 on the expression of CD80 on THP-1 cells.
FIG. 6C illustrates effects of DZ2002 on the expression of CD86 on THP-1 cells.
Figure 6:
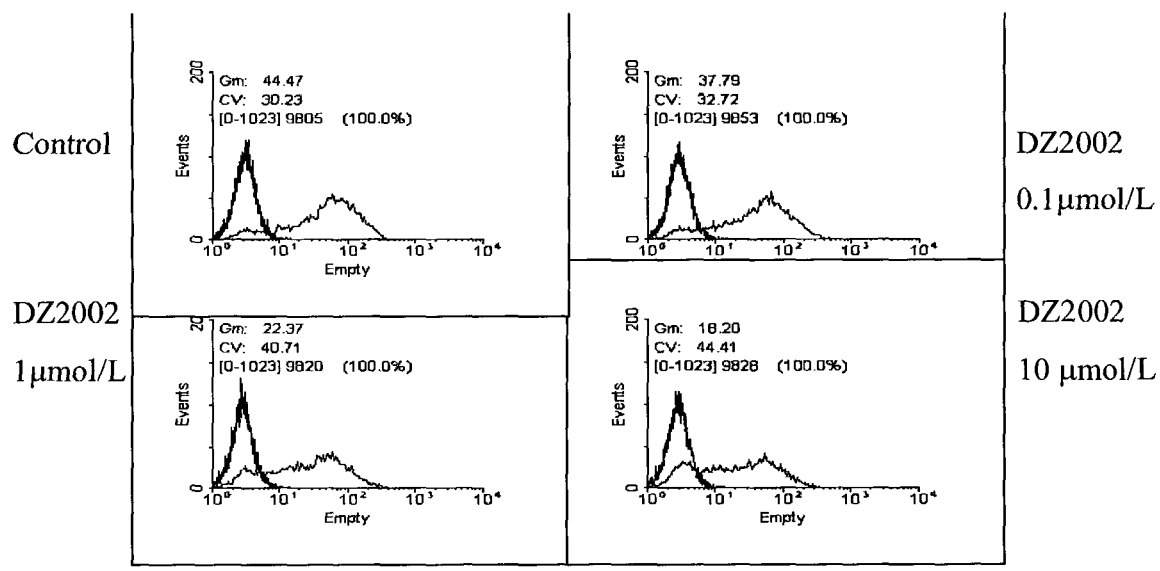

MHC-II, CD80 and CD86 expression by THP-1 cells was assessed following a 48-h incubation with media alone or with IFN-γ at 100 U/ml. Cells incubated with IFN-γ in the present of 10 μmol/L DZ2002 modestly reduce the levels of MHC-II expression of THP-1 cells and 0.1–10 μmol/L DZ2002 reduce the levels of CD80 and CD86 expression by an dose-dependently way. (FIG. 6A–C).

Effect of DZ2002 on IL-10, IL-12P40 and TNF-α Production From THP-1 Cells

Figure 7:
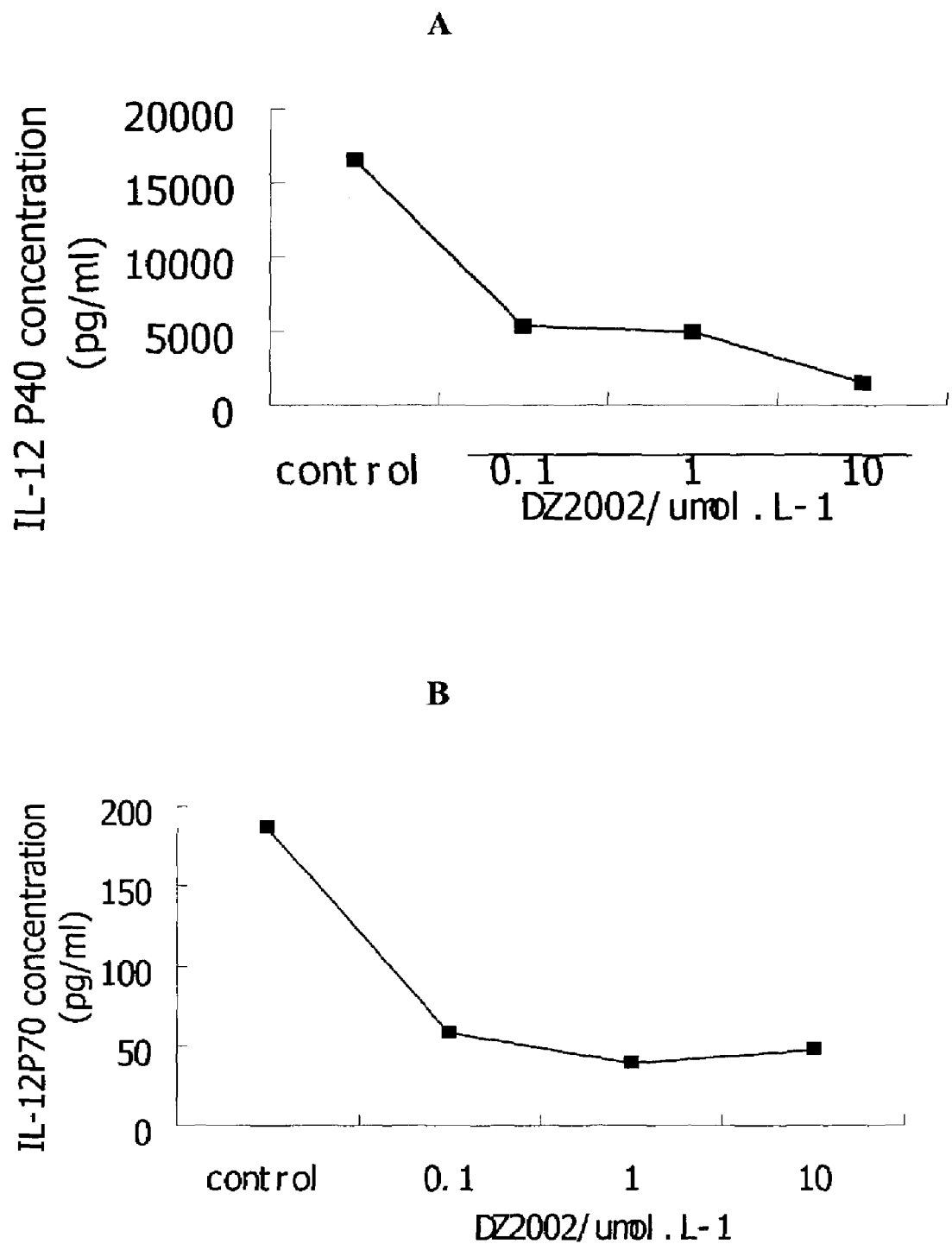
FIGS. 7A and 7B illustrate effects of DZ2002 on IL-12P40 and IL-12P70 production from THP-1 cells.
Figure 8:
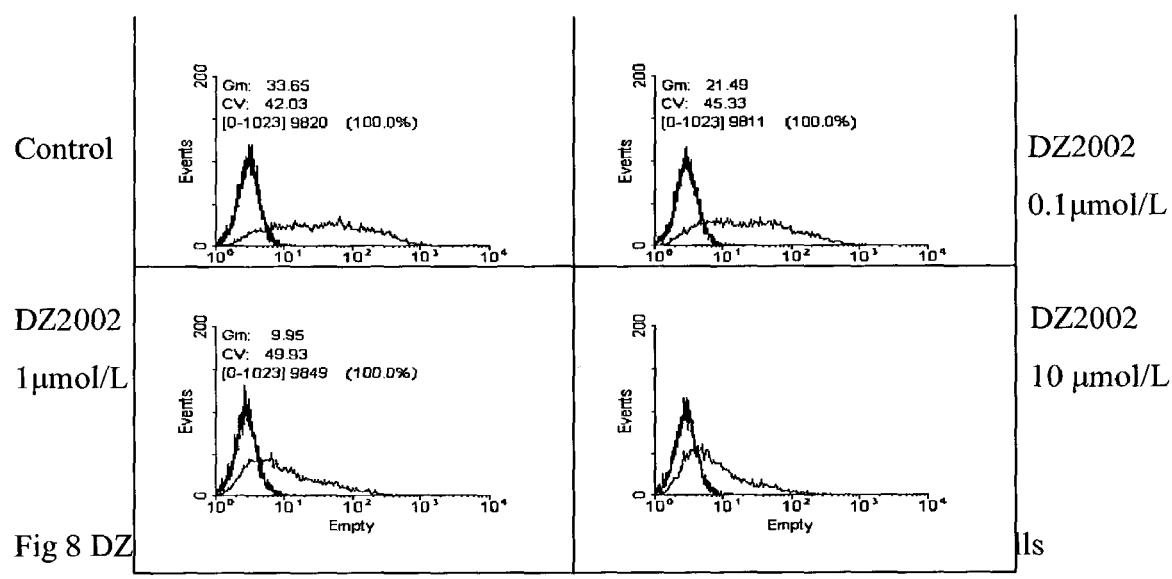

Cytokines produced by THP-1 cells were assessed following a 24-h incubation with IFN-γ at 500 U/ml and LPS at 1 μg/ml. As FIG. 7 shows, DZ2002 inhibited IL-12P40 and TNF-α release, in the dose of 0.1–10 μmol/L.

The above examples are included for illustrative purposes only and are not intended to limit the scope of the invention. Many variations to those described above are possible. Since modifications and variations to the examples described above will be apparent to those of skill in this art, it is intended that this invention be limited only by the scope of the appended claims.

What is claimed is:

1. A compound or a pharmaceutically acceptable salt thereof, having the formula (IA):

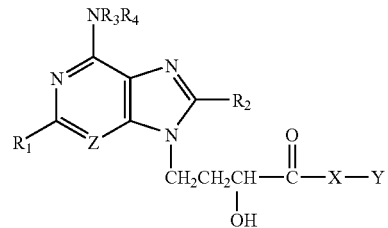

wherein R1 and R2 are the same or different, and are selected from the group consisting of hydrogen, hydroxy, unsubstituted alkyl, substituted alkyl, cycloalkyl, alkenyl, alkoxy, amino, aryl, heteroaryl, and halogen;

R3 and R4 are the same or different and are selected from the group consisting of hydrogen, unsubstituted alkyl, substituted alkyl, acetyl, alkenyl, aryl, and heteroaryl;

X is selected from the group consisting of oxygen, —NH, and sulfur; and

Y is selected from the group consisting of a $C_{1-10}$ unsubstituted alkyl group, a $C_{1-10}$ substituted alkyl group, alkenyl, vinyl, aryl, and heteroaryl, or formula (IB):

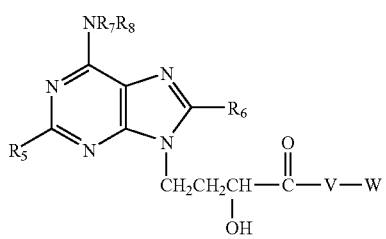

(IB)

wherein R5 is cycloalkyl, alkenyl or heteroaryl;

R6 is alkenyl or heteroaryl;

R7 and R8 are the same or different and are selected from the group consisting of hydrogen, unsubstituted alkyl, substituted alkyl, acetyl, alkenyl, aryl, and heteroaryl;

V is oxygen, —NH or sulfur;

and W is hydrogen, $C_{1-10}$ unsubstituted alkyl, $C_{1-10}$ substituted alkyl, alkenyl, vinyl, aryl, or heteroaryl.

2. The compound of claim 1, wherein in IA R1, R2, R3, and R4 are hydrogen.

3. The compound of claim 1, wherein in IA X is oxygen and in IB V is oxygen.

4. The compound of claim 1, wherein in IA Y is a C1–10 unsubstituted or substituted alkyl group and in IB W is a C1–10 unsubstituted or substituted alkyl group.

5. The compound of claim 1, wherein in IA R1, R2, R3, and R4 are hydrogen, X is oxygen, and Y is a C1–10 unsubstituted alkyl or a C1–10 substituted alkyl.

6. The compound of claim 1, wherein the β carbon relative to the COXY group of said compound has a S configuration.

7. The compound of claim 1, wherein the β carbon relative to the COXY group of said compound is a racemic mixture of S and R configurations.

8. A pharmaceutical composition comprising a compound of claim 1 and a pharmaceutically acceptable excipient.

9. The pharmaceutical composition of claim 8, wherein said composition is formulated for oral, parenteral, intranasal, topical, or injectable administration.

10. The pharmaceutical composition of claim 8, wherein said composition is formulated in a solid or liquid dosage form.

11. The pharmaceutical composition of claim 9, wherein said injectable administration is selected from the group consisting of intracavernous injection, subcutaneous injection, intravenous injection, intramuscular injection, and intradermal injection.

12. A kit, comprising an effective amount of said composition of claim 8, and an instruction means for administering said composition.

13. The compound of claim 1, wherein the β carbon relative to the COXY group of said compound has a R configuration.

* * * * *